US008481286B2

(12) United States Patent
Julien et al.

(10) Patent No.: US 8,481,286 B2
(45) Date of Patent: Jul. 9, 2013

(54) METHOD FOR PRODUCTION OF ISOPRENOID COMPOUNDS

(75) Inventors: Bryan Julien, Lexington, KY (US); Richard P. Burlingame, Nicholasville, KY (US)

(73) Assignee: Allylix, Inc., San Diego, CA (US)

( * ) Notice: Subject to any disclaimer, the term of this patent is extended or adjusted under 35 U.S.C. 154(b) by 566 days.

(21) Appl. No.: 12/540,094

(22) Filed: Aug. 12, 2009

(65) Prior Publication Data

US 2010/0151519 A1   Jun. 17, 2010

Related U.S. Application Data

(60) Provisional application No. 61/088,288, filed on Aug. 12, 2008.

(51) Int. Cl.
*C12P 21/00* (2006.01)
*C12P 19/34* (2006.01)
*C12P 5/00* (2006.01)
*C07H 21/04* (2006.01)

(52) U.S. Cl.
USPC ......... 435/69.1; 435/91.2; 435/166; 536/25.4

(58) Field of Classification Search
None
See application file for complete search history.

(56) References Cited

U.S. PATENT DOCUMENTS

| | | | |
|---|---|---|---|
| 4,745,051 A | 5/1988 | Smith et al. | 435/68 |
| 5,532,226 A | 7/1996 | Demarest et al. | 514/134 |
| 5,684,148 A | 11/1997 | Caruthers et al. | 536/26.1 |
| 5,824,774 A | 10/1998 | Chappell et al. | 530/350 |
| 5,962,674 A | 10/1999 | Iyer et al. | 536/25.34 |
| 6,001,982 A | 12/1999 | Ravikumar et al. | 536/22.1 |
| 6,031,092 A | 2/2000 | Just et al. | 536/25.34 |
| 6,072,045 A | 6/2000 | Chappell et al. | 536/23.1 |
| 6,242,227 B1 | 6/2001 | Millis et al. | 435/125 |
| 6,410,755 B1 | 6/2002 | Millis et al. | 549/408 |
| 6,531,303 B1 | 3/2003 | Millis et al. | 435/155 |
| 6,689,593 B2 | 2/2004 | Millis et al. | 435/155 |
| 7,186,891 B1 | 3/2007 | Chappell et al. | 800/298 |
| 7,273,735 B2 | 9/2007 | Schalk et al. | 435/166 |
| 7,622,614 B2 | 11/2009 | Julien et al. | 568/327 |
| 7,790,426 B2 | 9/2010 | Schalk et al. | 435/167 |
| 8,124,811 B2 | 2/2012 | Julien et al. | 568/367 |
| 2003/0157583 A1 | 8/2003 | Stevens et al. | 435/15 |
| 2004/0078840 A1 | 4/2004 | Chappell et al. | 800/278 |
| 2005/0210549 A1 | 9/2005 | Schalk et al. | 800/287 |
| 2006/0160172 A1 | 7/2006 | Hoshino et al. | 435/67 |
| 2006/0218661 A1 | 9/2006 | Chappell et al. | 800/278 |
| 2007/0031947 A1 | 2/2007 | Wallaart et al. | 435/119 |
| 2007/0231861 A1 | 10/2007 | Millis et al. | 435/69.1 |
| 2007/0238157 A1 | 10/2007 | Millis et al. | 435/166 |
| 2007/0238159 A1 | 10/2007 | Millis et al. | 435/252.33 |
| 2007/0238160 A1 | 10/2007 | Millis et al. | 435/252.33 |
| 2007/0254354 A1 | 11/2007 | Millis et al. | 435/252.33 |
| 2008/0171378 A1 | 7/2008 | Keasling | 435/254.21 |
| 2008/0178354 A1 | 7/2008 | Chappell et al. | 800/298 |
| 2008/0187983 A1 | 8/2008 | Dietrich et al. | 435/252.33 |
| 2008/0213832 A1 | 9/2008 | Schalk et al. | 435/69.1 |
| 2008/0233622 A1 | 9/2008 | Julien et al. | 435/148 |
| 2010/0035329 A1 | 2/2010 | Millis et al. | 435/254.2 |
| 2010/0151555 A1 | 6/2010 | Julien et al. | 435/193 |
| 2011/0318797 A1 | 12/2011 | Chappell et al. | 435/155 |
| 2012/0129235 A1 | 5/2012 | Julien et al. | 435/166 |

FOREIGN PATENT DOCUMENTS

| | | |
|---|---|---|
| WO | WO 96/39154 | 12/1996 |
| WO | WO 97/03211 | 1/1997 |
| WO | WO 97/38703 | 10/1997 |
| WO | 2004/031376 | 4/2004 |
| WO | WO 2006/014837 | 2/2006 |
| WO | WO 2006/102342 | 9/2006 |
| WO | WO 2006/134523 | 12/2006 |
| WO | WO 2012/058636 | 5/2012 |

OTHER PUBLICATIONS

Back et al., "Expression of a plant sesquiterpene cyclase gene in *Escherichia coil*," Arch. Biochem. Biophys. 315:527-532 (1994).
Greenhagen, "Origins of isoprenoid diversity: A study of structure-function relationships in sesquiterpene synthases," Dissertation, College of Agriculture at the University of Kentucky, 163 pages (2003).
Haralampidis et al., "Biosynthesis of triterpenoid saponins in plants," Adv. Biochem. Eng. Biotechnol. 75:31-49 (2002).
Jennings et al., "Molecular cloning and characterization of the yeast gene for squalene synthetase," Proc. Natl. Acad. Sci. U.S.A. 88:6038-6042 (1991).
Lesburg et al., "Managing and manipulating carbocations in biology: terpenoid cyclase structure and mechanism," Curr. Opin. Struc. Biol. 8:695-703 (1998).
Newman, J. and J. Chappell, "Isoprenoid biosynthesis in plants: carbon partitioning within the cytoplasmic pathway," Crit. Rev. Biochem. Mol. Biol. 34:95-106 (1999).
Park et al., "Metabolic engineering of *Saccharomyces cerevisiae* for the fermentative production of high-value terpenoid compounds," Abstract of presentation at Society for Industrial Microbiology Annual Meeting and Exhibition, Denver, CO (Jul. 30, 2007), 1 page.
Park et al., "Using *Saccharomyces cerevisiae* for production of terpenoid compounds for use as fragrances and flavorings," Abstract of presentation at Society for Industrial Microbiology Annual Meeting and Exhibition, San Diego, CA., Aug. 13, 2008, 1 page.
Takahashi et al., "Functional characterization of premnaspirodiene oxygenase, a cytochrome P450 catalyzing regio- and stereo-specific hydroxylations of diverse sesquiterpene substrates," J. Biol. Chem. 43:31744-31754 (2007).

(Continued)

*Primary Examiner* — Kagnew H Gebreyesus
(74) *Attorney, Agent, or Firm* — McKenna Long & Aldridge LLP; Stephanie Seidman

(57) ABSTRACT

The present invention is directed to variant squalene synthase enzymes, including *Saccharomyces cerevisiae* squalene synthase enzymes, and to nucleic acid molecules encoding these variant enzymes. These variant enzymes produce squalene at a lower rate than the wild-type enzyme, allowing more farnesyl pyrophosphate to be utilized for production of isoprenoid compounds, while still producing sufficient squalene to allow the *S. cerevisiae* cells to grow without the requirement for supplementation by sterols such as ergosterol. These variant enzymes, therefore, are highly suitable for the efficient production of isoprenoids.

49 Claims, 5 Drawing Sheets

OTHER PUBLICATIONS

UniProtKB P29704, "Squalene synthase,"[online] [retrieved on Oct. 18, 2011] [retrieved from the Internet:<URL: uniprot.org/uniprot/P29704]Integrated into UniProtKB/Swiss Prot: Apr. 1, 1993 [8 pages].

Zook et al., "Characterization of novel sesquiterpene biosynthesis in tobacco expressing fungal sesquiterpenoid synthase," Plant Physiol. 112:311-318 (1996).

International Preliminary Report on Patentability, issued Aug. 26, 2011, in connection with corresponding International Patent Application No. PCT/US09/53589, 20 pages.

Allylix, "Protein engineering and chembiosynthesis to produce novel sesquiterpenoids," Presentation at BIO World Congress on Industrial Biotechnology & Bioprocessing, Washington, D.C. (Jun. 28, 2010), 19 pages.

Madsen et al., "Linking genotype and phenotype of *Saccharomyces cerevisiae* strains reveals metabolic engineering targets and leads to triterpene hyper-producers," PLoS One 6(3):e14763 (2011) (14 pages).

Otero et al., "Whole genome sequencing of *Saccharomyces cerevisiae:* from genotype to phenotype for improved metabolic engineering applications," BMC Genomics 11:723 (2010) (17 pages).

Anderson et al., "Farnesyl diphosphate synthetase-molecular cloning sequence, and expression of an essential gene from *Saccharomyces cerevisiae*," J. Biol. Chem. 264:19176-19184 (1989).

Asadollahi et al., "Production of plant sesquiterpenes in *Saccharomyces cerevisiae:* effect of ERG9 repression on sesquiterpene biosynthesis," Biotechnol. Bioeng. 99:666-677 (2007).

ATCC Accession No. 37017, Retrieved from the Internet:<URL: atcc.org/ATCCAdvancedCatalogSearch/ProductDetails/tabid/452/Default.aspx, [retrieved on Apr. 28, 2010] [2 pages].

ATCC Accession No. 37092, Retrieved from the Internet:<URL: atcc.org/ATCCAdvancedCatalogSearch/ProductDetails/tabid/452/Default.aspx, [retrieved on Apr. 28, 2010] [2 pages].

ATCC Accession No. 53082, Retrieved from the Internet<URL: atcc.org/ATCCAdvancedCatalogSearch/ProductDetails/tabid/452/Default.aspx, [retrieved on Apr. 28, 2010] [2 pages].

Ausubel et al., "Current Protocols in Molecular Biology, vol. 2," Greene Pub. Assoc. & Wiley Interscience, Ch. 13 (1988).

Back, K. and J. Chappell, "Cloning and bacterial expression of a sesquiterpene cyclase from *Hyoscyamus muticus* and its molecular comparison to related terpene cyclases," J. Biol. Chem. 270(13):7375-7381 (1995).

Back, K. and J. Chappell, "Identifying functional domains within terpene cyclases using a domain-swapping strategy," Proc. Natl. Acad. Sci. U.S.A. 93:6841-6845 (1996).

Bauer et al., "A genetic enrichment for mutations constructed by oligodeoxynucleotide-directed mutagenesis," Gene 37:73-81 (1985).

Beier, D. and E. Young, "Characterization of a regulatory region upstream of the *ADR2* locus of *S. cerevisiae*," Nature 300:724-728 (1982).

Bitter, G., "Heterologous gene expression in yeast," Meth. Enzymol. 152:673-684 (1987).

Bitter et al., "Expression and secretion vectors for yeast," Meth. Enzymol. 153:516-544 (1987).

Bohlmann et al., "Plant terpenoid synthases: molecular biology and phylogenetic analysis," Proc. Natl. Acad. Sci. U.S.A. 95:4126-4133 (1998).

Brake, A., "Alpha-factor leader-directed secretion of heterologous proteins from yeast," Meth. Enzymol. 185:408-421 (1991).

Brisson et al., "Expression of a bacterial gene in plants by using a viral vector," Nature 310:511-514 (1984).

Broglie et al., "Light-regulated expression of a pea ribulose-1,5-bisphosphate carboxylase small subunit gene in transformed plant cells," Science 224:838-843 (1984).

Cane et al., "Trichodiene biosynthesis and the stereochemistry of the enzymatic cyclization of farnesyl pyrophosphate," Bioorg. Chem. 13:246-265 (1985).

Cane et al., "Aristolochene biosynthesis and enzymatic cyclization of farnesyl pyrophosphate," J. Am. Chem. Soc. 111:8914-8916 (1989).

Cane, D., "Enzymatic formation of sesquiterpenes," Chem. Rev. 90:1089-1103 (1990).

Cane et al., "Trichodiene synthase. Substrate specificity and inhibition," Biochem. 34:2471-2479 (1995).

Cane et al., "Trichodiene synthase. Identification of active site residues by site-directed mutagenesis," Biochem. 34:2480-2488 (1995).

Chang et al., "Phenotypic expression in *E. coli* of a DNA sequence coding for mouse dihydrofolate reductase," Nature 275:617-624 (1978).

Chappell, J., "Biochemistry and molecular biology of the isoprenoid biosynthetic pathway in plants," Annu. Rev. Plant Physiol. Plant Mol. Biol. 46:521-547 (1995).

Chappell et al., "Is the reaction catalyzed by 3-hydroxy-3-methylglutaryl coenzyme A reductase a rate-limiting step for isoprenoid biosynthesis in plants," Plant Physiol. 109:1337-1343 (1995).

Chappell, J., "The biochemistry and molecular biology of isoprenoid metabolism," Plant Physiol. 107:1-6 (1995).

Chappell, J., "The genetics and molecular genetics of terpene and sterol origami," Curr. Opin. Plant Biol. 5:151-157 (2002).

Chisholm et al., "Molecular and genetic approach to enhancing protein secretion," Meth. Enzymol. 185:471-482 (1991).

Colberre-Garapin et al., "A new dominant hybrid selective marker for higher eukaryotic cells," J. Mol. Biol. 150:1-14 (1981).

Cone, R. and R. Mulligan, "High-efficiency gene transfer into mammalian genes: generation of helper-free recombinant retrovirus with broad mammalian host range," Proc. Natl. Acad. Sci. U.S.A. 81:6349-6353 (1984).

Coruzzi et al., "Tissue-specific and light-regulated expression of a pea nuclear gene encoding the small subunit of ribulose-1,5-bisphosphate carboxylase," EMBO J. 3:1671-1679 (1984).

Craik, C., "Use of oligonucleotides for site-specific mutagenesis," BioTechniques Jan./Feb., pp. 12-19 (1985).

Deshpande, M., "Ethanol production from cellulose by coupled saccharification/fermentation using *Saccharomyces cerevisiae* and cellulase complex from *Sclerotiun rolfsii* UV-8 mutant," Appl. Biochem. Biotechnol. 36:227-234 (1992).

Devarenne et al., "Molecular characterization of tobacco squalene synthase and regulation in response to fungal elicitor," Arch. Biochem. Biophys. 349:205-215 (1998).

Devarenne et al., "Regulation of squalene synthase, a key enzyme of sterol biosynthesis, in tobacco," Plant Physiol. 129:1095-1106 (2002).

Donahue, T. and A. Cigan, "Sequence and structural requirements for efficient translation in yeast," Meth. Enzymol. 185:366-372 (1991).

Dudareva et al., "Biochemistry of plant volatiles," Plant Physiol. 135:1893-1902 (2004).

Emr, S., "Heterologous gene expression in yeast," Meth. Enzymol. 185:231-233 (1991).

Etcheverry, T., "Induced expression using yeast copper metallothionein promoter," Meth. Enzymol. 185:319-329 (1991).

Facchini, P. and J. Chappell, "Gene family for an elicitor-induced sesquiterpene cyclase in tobacco," Proc. Natl. Acad. Sci. U.S.A. 89:11088-11092 (1992).

Fleer et al., "High-level secretion of correctly processed recombinant human interleukin-1β in *Kluyveromyces lactis*," Gene 107:285-295 (1991).

Goeddel et al., "Direct expression in *Escherichia coli* of a DNA sequence coding for human growth hormone," Nature 281:544-548 (1979).

Goeddel et al., "Synthesis of human fibroblast interferon by *E. coli*," Nucleic Acids Res. 8:4057-4074 (1980).

Greenhagen, B. and J. Chappell, "Molecular scaffolds for chemical wizardry: learning nature's rules for terpene cyclases," Proc. Natl. Acad. Sci. U.S.A. 98(24):13479-13491 (2001).

Greenhagen et al., "Identifying and manipulating structural determinates linking catalytic specificities in terpene synthases," Proc. Natl. Acad. Sci. U.S.A. 103(26):9826-9831 (2006).

Greenhagen et al., "Probing sesquiterpene hydroxylase activities in a coupled assay with terpene synthases," Arch. Biochem. Biophys. 409:385-394 (2003).

Gurley et al., "Upstream sequences required for efficient expression of a soybean heat shock gene," Mol. Cell. Biol. 6(2):559-565 (1986).

Hanley, K. and J. Chappell, "Solubilization, partial purification, and immunodetection of squalene synthetase from tobacco cell suspension cultures," Plant Physiol. 98:215-220 (1992).

Hartman, S. and R. Mulligan, "Two dominant-acting selectable markers for gene transfer studies in mammalian cells," Proc. Natl. Acad. Sci. U.S.A. 85:8047-8051 (1988).

Hess et al., "Cooperation of glycolytic enzymes," Adv. Enzyme Reg. 7:149-167 (1969).

Hitzeman et al., "Isolation and characterization of the yeast 3-phosphoglycerokinase gene (PGK) by an immunological screening technique," J. Biol. Chem. 255(24):12073-12080 (1980).

Hitzeman et al., "Use of heterologous and homologous signal sequences for secretion of heterologous proteins from yeast," Meth. Enzymol. 185:421-440 (1991).

Holland, M. and J. Holland, "Isolation and identification of yeast messenger ribonucleic acids coding for enolase, glyceraldehyde-3-phosphate dehydrogenase, and phosphoglycerate kinase," Biochem. 17:4900-4907 (1978).

Inouye, S. and M. Inouye, "Up-promoter mutations in the 1pp gene of *Escherichia coli*," Nucleic Acids Res. 13(9):3101-3109 (1985).

Jaye et al., "Isolation of a human anti-haemophilic factor IX cDNA clone using a unique 52-base synthetic oligonucleotide probe deduced from the amino acid sequence of bovine factor IX," Nucleic Acids Res. 11(8):2325-2335 (1983).

Joly, A. and P. Edwards, "Effect of site-directed mutagenesis of conserved aspartate and arginine residues upon farnesyl diphosphate synthase activity," J. Biol. Chem. 268(36):26983-26989 (1993).

Jones, E., "Vacuolar proteases in yeast *Saccharomyces cerevisiae*," Meth. Enzymol. 185:372-386 (1991).

Kendall et al., "Cotranslation amino-terminal processing," Meth. Enzymol. 185:398-407 (1991).

Kingsman et al., "High efficiency yeast expression vectors based on the promoter of the phosphoglycerate kinase gene," Meth. Enzymol. 185:329-341 (1991).

Kunkel et al., "Rapid and efficient site-specific mutagenesis without phenotypic selection," Meth. Enzymol. 154:367-382 (1987).

Kunkel, T., "Rapid and efficient site-specific mutagenesis without phenotypic selection," Proc. Natl. Acad. Sci. U.S.A. 82:488-492 (1985).

Logan, J. and T. Shenk, "Adenovirus tripartite leader sequence enhances translation of mRNAs late after infection," Proc. Natl. Acad. Sci. U.S.A. 81:3655-3659 (1984).

Lowy et al., "Isolation of transforming DNA: cloning the hamster aprt gene," Cell 22:817-823 (1980).

Mackett et al., "General method for production and selection of infectious vaccinia virus recombinants expressing foreign genes," J. Virol. 49(3):857-864 (1984).

Mackett et al., "Vaccinia virus: a selectable eukaryotic cloning and expression vector," Proc. Natl. Acad. Sci. U.S.A. 79:7415-7419 (1982).

Maniatis, T., "Molecular Cloning: A Laboratory Manual," Cold Spring Harbor Laboratory, p. 412 (1982).

Mata et al., "A hexameric phosphorothioate oligonucleotide telomerase inhibitor arrests growth of Burkitt's lymphoma cells in vitro and in vivo," Toxicol. Appl. Pharmacol. 144:189-197 (1997).

Milligan et al., "Current concepts in antisense drug design," J. Med. Chem. 36(14):1923-1937 (1993).

Mulligan, R. and P. Berg, "Selection for animal cells that express the *Escherichia coli* gene coding for xanthine-guanine phosphoribosyltransferase," Proc. Natl. Acad. Sci. U.S.A. 78(4):2072-2076 (1981).

Mylin et al., "Regulated *GAL4* expression cassette providing controllable and high level output from high copy galactose promoters in yeast," Meth. Enzymol. 185:297-308 (1991).

Needleman, S. and C. Wunsch, "A general method applicable to the search for similarities in the amino acid sequence of two proteins," J. Mol. Biol. 48:443-453 (1970).

O'Hare et al., "Transformation of mouse fibroblasts to methotrexate resistance by a recombinant plasmid expressing a prokaryotic dihydrofolate reductase," Proc. Natl. Acad. Sci. U.S.A. 78(3):1527-1531 (1981).

Okada et al., "Characterization of botryococcene synthase enzyme activity, a squalene synthase-like activity from the green microalga *Botryococcus braunii*, race B," Arch. Biochem. Biophys. 422:110-118 (2004).

Okada et al., "Molecular characterization of squalene synthase from the green microalga *Botryococcus braunii*, race B," Arch. Biochem. Biophys. 373:307-317 (2000).

Panicali, D. and E. Paoletti, "Construction of poxviruses as cloning vectors: insertion of the thymidine kinase gene from herpes simplex virus into the DNA of infectious vaccinia virus," Proc. Natl. Acad. Sci. U.S.A. 79:4927-4931 (1982).

Paradise et al., "Redirection of flux through the Fpp branch-point in *Saccharaomyces cerevisiae* by down-regulating squalene synthase," Biotechnol. Bioeng. 100:371-378 (2008).

Price et al., "Expression of heterologous proteins in *Saccharomyces cerevisiae* using the ADH2 promoter," Meth. Enzymol. 185:308-318 (1991).

Ro et al., "Production of the antimalarial drug precursor artemisinic acid in engineered yeast," Nature 440:940-943 (2006).

Rose, A. and J. Broach, "Propagation and expression of cloned genes in yeast: 2um circle based vectors," Meth. Enzymol. 185:234-279 (1991).

Rosenberg et al., "Glyceraldehyde-3-phosphate dehydrogenase-derived expression cassettes for constitutive synthesis of heterologous proteins," Meth. Enzymol. 185:341-350 (1991).

Rothstein, R., "Cloning in yeast," in, *"DNA Cloning, vol. II,"* Glover, D. (Ed.), IRL Press, Wash., D.C., Ch. 3, pp. 45-67 (1986).

Russell et al., "Nucleotide sequence of the yeast alcohol dehydrogenase II gene," J. Biol. Chem. 258:2674-2682 (1982).

Rüther, U. and B. Müller-Hill, "Easy identification of cDNA clones," EMBO J. 2(10):1791-1794 (1983).

Samstag et al., "Synthesis and properties of new antisense oligodeoxynucleotides containing benzylphosphonate linkages," Antisense Nucleic Acid Drug Dev. 6:153-156 (1996).

Santerre et al., "Expression of prokaryotic genes for hygromycin B and G418 resistance as dominant-selection markers in mouse L cells," Gene 30:147-156 (1984).

Sarver et al., "Bovine papilloma virus deoxyribonucleic acid: a novel eukaryotic cloning vector," Mol. Cell. Biol. 1(6):486-496 (1981).

Sledziewski et al., "Superimposition of temperature regulation on yeast promoters," Meth. Enzymol. 185:351-366 (1991).

Smith et al., "Molecular engineering of the *Autographa californica* nuclear polyhedrosis virus genome: deletion mutations within the polyhedrin gene," J. Virol. 46(2):584-593 (1983).

Smith, D. and K. Johnson, "Single-step purification of polypeptides expressed in *Escherichia coli* as fusions with glutathione S-transferase," Gene 67:31-40 (1998).

Song, L. and C. Poulter, "Yeast farnesyl-diphosphate synthase: site-directed mutagenesis of residues in highly conserved prenyltransferase domains I and II," Proc. Natl. Acad. Sci. U.S.A. 91:3044-3048 (1994).

Stearns et al., "Manipulating yeast genome using plasmid vectors," Meth. Enzymol. 185:280-297 (1991).

Strauss-Soukup et al., "Effects of neutralization pattern and sterochemistry on DNA bending by methylphosphonate substitutions," Biochem. 36:8692-8698 (1997).

Studier, F. and B. Moffatt, "Use of bacteriophage T7 RNA polymerase to direct selective high-level expression of cloned genes," J. Mol. Biol. 189:113-130 (1986).

Szybalska, E. and W. Szybalski, "Genetics of human cell lines, IV. DNA-mediated heritable transformation of a biochemical trait," Proc. Natl. Acad. Sci. U.S.A. 48:2026-2034 (1962).

Takahasi et al., "Metabolic engineering of sesquiterpene metabolism in yeast," Biotechnol. Bioeng. 97:170-181 (2007).

Takamatsu et al., "Expression of bacterial chloramphenicol acetyltransferase gene in tobacco plants mediated by TMV-RNA," EMBO J. 6(2):307-311 (1987).

Thai et al., "Farnesol is utilized for isoprenoid biosynthesis in plant cells via farnesyl pyrophosphate formed by successive monophosphorylation reactions," Proc. Natl. Acad. Sci. U.S.A. 96(23):13080-13085 (1999).

van den Berg et al., "Kluyveromyces as a host for heterologous gene expression: expression and secretion of prochymosin," Biotechnol. 8:135-139 (1990).

Van Heeke, G. and S. Schuster, "Expression of human asparagine synthetase in *Escherichia coli*," J. Biol. Chem. 264(10):5503-5509 (1989).

Vögeli, U. and J. Chappell, "Induction of sesquiterpene cyclase and suppression of squalene synthetase activities in plant cell cultures treated with fungal elicitor," Plant Physiol. 88:1291-1296 (1988).

Walder, R. and J. Walder, "Oligodeoxynucleotide-directed mutagenesis using the yeast transformation system," Gene 42:133-139 (1986).

Watson et al., "Molecular Biology of the Gene," 4th Edition, Benjamin/Cummings, p. 224 (1987).

Weissbach, A. and H. Weissbach (Eds.), "Methods for Plant Molecular Biology, Section VIII," Academic Press: NY, pp. 421-463 (1988).

Wendt et al., "Structure and function of a squalene cyclase," Science 277:1811-1815 (1997).

Wigler et al., "Transfer of purified herpes simplex virus thymidine kinase gene to cultured mouse cells," Cell 11:223-232 (1977).

Wigler et al., "Transformation of mammalian cells with an amplifiable dominant-acting gene," Proc. Natl. Acad. Sci. U.S.A. 77(6):3567-3570 (1980).

Wilkinson, K., "Detection and inhibition of ubiquitin-dependent proteolysis," Meth. Enzymol. 185:387-397 (1991).

Wu et al., "Redirection of cytosolic or plastidic isoprenoid precursors elevates terpene production in plants," Nat. Biotechnol. 24(11):1441-1447 (2006).

Yoshioka et al., "cDNA cloning of sesquiterpene cyclase and squalene synthase, and expression of the genes in potato tuber infected with *Phytophthora infestans*," Plant Cell. Physiol. 40:993-998 (1999).

Fegueur et al., "Isolation and primary structure of the ERG9 gene of *Saccharomyces cerevisiae* encoding squalene synthetase," Curr. Genet. 20(5):365-372 (1991).

Genbank Accession No. ADB55710.1, "(−)-ent-kaurene synthase [*Picea sitchensis* ]," Published on May 3, 2010 [online][retrieved on Mar. 19, 2012] Retrieved from:<URL:ncbi.nlm.nih.gov/protein/ADB55710.1, 2 pages.

Office Action, issued Nov. 25, 2011, in connection with corresponding U.S. Appl. No. 12/540,050, 9 pages.

Extended European Search Report, issued Apr. 16, 2012, in connection with corresponding European Patent Application No. 09807243.2, 11 pages.

```
              10         20         30         40         50
     GCCCATCTTCAACAACAATACCGACTTACCATCCTATTTGCTTTGCCCTTTT
        7-162.1
        60         70         80         90        100
     TCTTTTCCACTGCACTTTGCATCGGAAGGCGTTATCGGTTTTGGGTTTAGTG 110        120        130        140        150
     CCTAAACGAGCAGCGAGAACACGACCACGGGCTATATAAATGGAAAGTTAGG 160        170        180        190        200
     ACAGGGGCAAAGAATAAGAGCACAGAAGAAGAGAAAAGACGAAGAGCAGAAG 210        220        230        240        250        260
     CGGAAAACGTATACACGTCACATATCACACACACAATGGGAAAGCTATTA
                                           M  G  K  L  L>

270        280        290        300        310
     CAATTGGCATTGCATCCGGTCGAGATGAAGGCAGCTTTGAAGCTGAAGTTTT
       Q  L  A  L  H  P  V  E  M  K  A  A  L  K  L  K  F>

320        330        340        350        360
     GCAGAACACCGCTATTCTCCATCTATGATCAGTCCACGTCTCCATATCTCTT
       C  R  T  P  L  F  S  I  Y  D  Q  S  T  S  P  Y  L  L 370        380        390        400        410
     GCACTGTTTCGAACTGTTGAACTTGACCTCCAGATCGTTTGCTGCTGTGATC
       H  C  F  E  L  L  N  L  T  S  R  S  F  A  A  V  I>

420        430        440        450        460
     AGAGAGCTGCATCCAGAATTGAGAAACTGTGTTACTCTCTTTTATTTGATTT
       R  E  L  H  P  E  L  R  N  C  V  T  L  F  Y  L  I>

470        480        490        500        510        520
     TAAGGGCTTTGGATACCATCGAAGACGATATGTCCATCGAACACGATTTGAA
       L  R  A  L  D  T  I  E  D  D  M  S  I  E  H  D  L  K>

530        540        550        560        570
     AATTGACTTGTTGCGTCACTTCCACGAGAAATTGTTGTTAACTAAATGGAGT
       I  D  L  L  R  H  F  H  E  K  L  L  L  T  K  W  S>
```

FIGURE 2A

```
        580       590       600       610       620
TTCGACGGAAATGCCCCCGATGTGAAGGACAGAGCCGTTTTGACAGATTTCG
 F  D  G  N  A  P  D  V  K  D  R  A  V  L  T  D  F>

630       640       650       660       670
AATCGATTCTTATTGAATTCCACAAATTGAAACCAGAATATCAAGAAGTCAT
 E  S  I  L  I  E  F  H  K  L  K  P  E  Y  Q  E  V  I>

680       690       700       710       720
CAAGGAGATCACCGAGAAAATGGGTAATGGTATGGCCGACTACATCTTAGAT
 K  E  I  T  E  K  M  G  N  G  M  A  D  Y  I  L  D>

730       740       750       760       770       780
GAAAATTACAACTTGAATGGGTTGCAAACCGTCCACGACTACGACGTGTACT
 E  N  Y  N  L  N  G  L  Q  T  V  H  D  Y  D  V  Y>

790       800       810       820       830
 GTCACTACGTAGCTGGTTTGGTCGGTGATGGTTTGACCCGTTTGATTGTCAT
  C  H  Y  V  A  G  L  V  G  D  G  L  T  R  L  I  V  I>

840       850       860       870       880
TGCCAAGTTTGCCAACGAATCTTTGTATTCTAATGAGCAATTGTATGAAAGC
 A  K  F  A  N  E  S  L  Y  S  N  E  Q  L  Y  E  S>

890       900       910       920       930
ATGGGTCTTTTCCTACAAAAAACCAACATCATCAGAGATTACAATGAAGATT
 M  G  L  F  L  Q  K  T  N  I  I  R  D  Y  N  E  D>

940       950       960       970       980
TGGTCGATGGTAGATCCTTCTGGCCCAAGGAAATCTGGTCACAATACGCTCC
 L  V  D  G  R  S  F  W  P  K  E  I  W  S  Q  Y  A  P>

990       1000      1010      1020      1030      1040
TCAGTTGAAGGACTTCATGAAACCTGAAAACGAACAACTGGGGTTGGACTGT
 Q  L  K  D  F  M  K  P  E  N  E  Q  L  G  L  D  C>

1050      1060      1070      1080      1090
ATAAACCACCTCGTCTTAAACGCATTGAGTCATGTTATCGATGTGTTGACTT
 I  N  H  L  V  L  N  A  L  S  H  V  I  D  V  L  T>
```

FIGURE 2B

```
              1100       1110       1120       1130       1140
         ATTTGGCCGGTATCCACGAGCAATCCACTTTCCAATTTTGTGCCATTCCCCA
          Y  L  A  G  I  H  E  Q  S  T  F  Q  F  C  A  I  P  Q>

1150       1160       1170       1180       1190
         AGTTATGGCCATTGCAACCTTGGCTTTGGTATTCAACAACCGTGAAGTGCTA
          V  M  A  I  A  T  L  A  L  V  F  N  N  R  E  V  L>

1200       1210       1220       1230       1240
         CATGGCAATGTAAAGATTCGTAAGGGTACTACCTGCTATTTAATTTTGAAAT
          H  G  N  V  K  I  R  K  G  T  T  C  Y  L  I  L  K>

1250       1260       1270       1280       1290       1300
    CAAGGACTTTGCGTGGCTGTGTCGAGATTTTTGACTATTACTTACGTGATAT
     S  R  T  L  R  G  C  V  E  I  F  D  Y  Y  L  R  D  I>

1310       1320       1330       1340       1350
         CAAATCTAAATTGGCTGTGCAAGATCCAAATTTCTTAAAATTGAACATTCAA
          K  S  K  L  A  V  Q  D  P  N  F  L  K  L  N  I  Q>

1360       1370       1380       1390       1400
         ATCTCCAAGATCGAACAGTTTATGGAAGAAATGTACCAGGATAAATTACCTC
          I  S  K  I  E  Q  F  M  E  E  M  Y  Q  D  K  L  P>

1410       1420       1430       1440       1450
         CTAACGTGAAGCCAAATGAAACTCCAATTTTCTTGAAAGTTAAAGAAAGATC
          P  N  V  K  P  N  E  T  P  I  F  L  K  V  K  E  R  S>

1460       1470       1480       1490       1500
         CAGATACGATGATGAATTGGTTCCAACCCAACAAGAAGAAGAGTACAAGTTC
          R  Y  D  D  E  L  V  P  T  Q  Q  E  E  E  Y  K  F>

1510       1520       1530       1540       1550       1560
    AATATGGTTTTATCTATCATCTTGTCCGTTCTTCTTGGGTTTTATTATATAT
     N  M  V  L  S  I  I  L  S  V  L  L  G  F  Y  Y  I>

1570       1580       1590       1600       1610
         ACACTTTACACAGAGCGTGAAGTCTGCGCCAAATAACATAAACAAACAACTC
```

FIGURE 2C

```
Y  T  L  H  R  A  *
   1620     1630
CGAACAATAACTAAGTACT
      7-162.2
```

FIGURE 2D

METHOD FOR PRODUCTION OF ISOPRENOID COMPOUNDS

CROSS-REFERENCE

This application claims the benefit of priority to U.S. Provisional Application Ser. No. 61/088,288, filed Aug. 12, 2008, which is incorporated herein in its entirety.

FIELD OF THE INVENTION

This invention is directed to yeast strains that overproduce a precursor to terpenes, farnesyl pyrophosphate (FPP), and are capable of growing without sterol supplementation.

BACKGROUND OF THE INVENTION

With over 50,000 identified members, terpenoids comprise the largest known class of natural products. These compounds are structurally diverse, although based on related carbon skeletons. The structural diversity found among these compounds allows them to perform a variety of essential biochemical functions. These compounds serve as attractants for pollinators, antimicrobial and antiherbivorial defense compounds, and may react with reactive oxygen species to protect against oxidative damage (Dudereva et al., Plant Physiol. 135: 1893-1902 (2004)). As components of the essential oils of aromatic plants, they are largely responsible for the distinct flavors and fragrances associated with their host plants. Moreover, the value of these small molecules extends beyond their biological utility. Many terpenoids have commercial value as antibiotics, pest control agents, fragrances, flavors, and anti-cancer agents, among other important uses.

A specific class of these natural products, sesquiterpenoids, is derived from a common 15-carbon building block. This common 15-carbon building block is farnesyl pyrophosphate (FPP). Many important products, such as the flavoring nootkatone, the cosmetic additive bisabolol, and amorpha-4,11-diene, a precursor to the antimalarial compound artemisinin, are sesquiterpenoids and thus are based on the 15-carbon skeleton of FPP. Therefore, methods that can increase the yield of FPP that can be utilized in sesquiterpenoid synthesis are of extreme importance.

To maximize production of terpenes, mutations in squalene synthase have been used to prevent or minimize conversion of farnesyl pyrophosphate to squalene. In practice, this has been done by either eliminating the corresponding gene, reducing its expression using weak promoters, or controlling its expression with a regulated promoter. Squalene is a precursor to sterols, which are essential to viability of yeast and other organisms. Accordingly, complete elimination of the gene requires feeding of sterols. The yeast *Saccharomyces cerevisiae* is not normally capable of taking up sterols under aerobic conditions, so in order to feed sterols to mutants, secondary mutations enabling sterol uptake are required.

Various solutions have been proposed in order to obtain high yields of farnesyl pyrophosphate for maximum production of terpenes. In one approach, the ERG9 gene of the yeast is completely eliminated. The gene ERG9 encodes the enzyme squalene synthase. However, because these mutants in which ERG9 is eliminated cannot synthesize squalene, which is a precursor to sterols, they must be fed sterols (Takahashi, et al. Biotech. Bioengineer. 97:170-181 (2007)). In another approach, PCT Patent Application Publication No. WO 06/102342 by Bailey et al. describes production of high yields of farnesyl pyrophosphate by modifying the expression or activity of one or more polypeptides involved in generating cytosolic acetyl-CoA and/or NADPH. In another approach, a promoter, the MET3 promoter, is used in place of the native ERG9 promoter to downregulate the expression of squalene synthase by repressing its synthesis by adding methionine, which acts as a repressor with respect to the MET3 promoter (Asadollahi et al., Biotech. Bioengineer. 99: 666-677 (2007)). In a similar approach, in addition to repression of ERG9 production, overproduction of a soluble, truncated form of 3-hydroxy-3-methylglutaryl-coenzyme A reductase, and enhancement of the activity of the transcription factor UPC2 was employed (Paradise et al., Cell. Metabol. Engineer. Bioengineer. 100: 371-378 (2008); Ro et al., Nature 440: 940-943 (2006)).

However, there is a need for improved strains of *Saccharomyces cerevisiae* that can overproduce FPP without the need for sterol supplementation and without regulating expression. Preferably, these improved strains would grow efficiently and produce high levels of farnesyl pyrophosphate for subsequent terpenoid synthesis.

SUMMARY OF THE INVENTION

A number of mutations of the *Saccharomyces cerevisiae* squalene synthase gene have been isolated and characterized. These mutants produce a sufficient quantity of squalene synthesis enzyme so that the enzyme catalyzes the synthesis of squalene at a sufficiently high rate so that sterol supplementation for the *S. cerevisiae* cells is not required, while having reduced activity so that more farnesyl pyrophosphate is available for isoprenoid biosynthesis. The reduced activity may be the result of reduced catalytic efficiency of the enzyme, or of reduced intracellular concentration of the protein, or both.

Accordingly, one aspect of the present invention is an isolated nucleic acid molecule that encodes a squalene synthase enzyme that, when present and expressed in vivo in a eukaryotic microbial host as the only squalene synthase species, catalyzes the synthesis of squalene at a sufficiently high rate so that supplementation of the eukaryotic microbial host with a sterol is not required for growth, and also has a reduced squalene synthase activity (referred to herein for convenience as a variant squalene synthase enzyme). In one alternative, a host cell containing the nucleic acid molecule, when expressed in vivo, produces a greater concentration of an isoprenoid in grams of isoprenoid per liter of culture than a corresponding host containing a wild-type nucleic acid molecule.

The variant squalene synthase enzyme of the present invention can be a squalene synthase enzyme of any suitable species. In one aspect, variant squalene synthase enzymes are from *Saccharomyces cerevisiae*.

Isolated nucleic acid molecules encoding a variant *S. cerevisiae* squalene synthase enzyme according to the present invention include, but are not limited to, the following isolated nucleic acid molecules:

(1) an isolated nucleic acid molecule encoding a variant *S. cerevisiae* squalene synthase enzyme, in which the following nucleic acid changes occur: (a) 691 A→G, resulting in the amino acid change E→G at amino acid residue 149; (b) 748 G→T, resulting in the amino acid change G→V at amino acid residue 168; (c) 786 T→A, resulting in the amino acid change Y→N at amino acid residue 181; (d) 1114 A→T, resulting in the amino acid change Q→L at amino acid residue 290; (e) 1213 T→C, resulting in the amino acid change I→T at amino acid residue 323; and (f) 1290 T→C, resulting in no change of the amino acid L at amino acid residue 349 (silent mutation);

(2) an isolated nucleic acid molecule encoding a variant *S. cerevisiae* squalene synthase enzyme, in which the following nucleic acid changes occur: (a) 72 C→A (in the non-coding region); (b) 110 ΔA (in the non-coding region); and (c) 801 G→A, resulting in the amino acid change V→I at amino acid residue 186;

(3) an isolated nucleic acid molecule encoding a variant *S. cerevisiae* squalene synthase enzyme, in which the following nucleic acid changes occur: (a) 989 T→A, resulting in no change of the amino acid P at amino acid residue 248 (silent mutation); (h) 1112 G→A, resulting in no change of the amino acid E at amino acid residue 289 (silent mutation); (c) 1220 G→A, resulting in no change of the amino acid K at amino acid residue 325 (silent mutation); and (d) 1233 T→C, resulting in the amino acid change Y→H at amino acid residue 330;

(4) an isolated nucleic acid molecule encoding a variant *S. cerevisiae* squalene synthase enzyme, in which the following nucleic acid changes occur: (a) 786 T→A, resulting in the amino acid change Y→N at amino acid residue 181; (b) 1025 A→G, resulting in no change of the amino acid Q at amino acid residue 260 (silent mutation); (c) 1056 T→A, resulting in the amino acid change L→I at amino acid residue 271; (d) 1068 A→G, resulting in the amino acid change S→G at amino acid residue 275; and (e) 1203 A→G, resulting in the amino acid change N→D at amino acid residue 320;

(5) an isolated nucleic acid molecule encoding a variant *S. cerevisiae* squalene synthase enzyme, in which the following nucleic acid changes occur: (a) 886 T→C, resulting in the amino acid change M→T at amino acid residue 214; (b) 969 A→G, resulting in the amino acid change I→V at amino acid residue 242; (c) 1075 T→C, resulting in the amino acid change V→A at amino acid residue 277; and (d) 1114 A→T, resulting in the amino acid change Q→L at amino acid residue 290;

(6) an isolated nucleic acid molecule encoding a variant *S. cerevisiae* squalene synthase enzyme, in which the following nucleic acid changes occur: 84 T→A (in the non-coding region); (b) 283 A→T, resulting in the amino acid change E→V at amino acid residue 13; (c) 424 T→C, resulting in the amino acid change L→P at amino acid residue 60; (d) 440 A→G, resulting in no change of the amino acid R at amino acid residue 65 (silent mutation); and (e) 1076 T→C, resulting in no change of the amino acid V at amino acid residue 277 (silent mutation);

(7) an isolated nucleic acid molecule encoding a variant *S. cerevisiae* squalene synthase enzyme, in which the following nucleic acid changes occur: (a) 619 A→T, resulting in the amino acid change D→V at amino acid residue 125; (b) 634 T→C, resulting in the amino acid change L→P at amino acid residue 130; and (c) 962 C→T, resulting in no change of the amino acid P at amino acid residue 239 (silent mutation);

(8) an isolated nucleic acid molecule encoding a variant *S. cerevisiae* squalene synthase enzyme, in which the following nucleic acid changes occur: (a) 150 A→T (in the non-coding region); (b) 410 T→G, resulting in no change of the amino acid A at amino acid residue 55 (silent mutation); (c) 411 G→T, resulting in the amino acid change V→L at amino acid residue 56; and (d) 1248 T→C, resulting in the amino acid change S→P at amino acid residue 335;

(9) an isolated nucleic acid molecule encoding a variant *S. cerevisiae* squalene synthase enzyme, in which the following nucleic acid changes occur: (a) 510 C→T, resulting in the amino acid change H→Y at amino acid residue 89; (b) 573 T→C, resulting in the amino acid change F→L at amino acid residue 110; (c) 918 A→G, resulting in the amino acid change R→G at amino acid residue 224; and (d) 997 A→G, resulting in the amino acid change K→G at amino acid residue 251;

(10) an isolated nucleic acid molecule identical to any of (3), (4), (6), (7), or (8), above, except that one or more of the silent mutations in nucleic acid molecules (3), (4), (6), (7), or (8) are omitted;

(11) an isolated nucleic acid molecule encoding a variant *S. cerevisiae* squalene synthase enzyme in which the wild-type *S. cerevisiae* squalene synthase enzyme is mutated with the same amino acid changes as in any of (1) through (10) above;

(12) an isolated nucleic acid molecule encoding a variant *S. cerevisiae* squalene synthase enzyme containing any of the amino acid changes in any of (1) through (10) above; and

(13) an isolated nucleic acid molecule encoding a variant *S. cerevisiae* squalene synthase enzyme in which the squalene synthase enzyme differs from the squalene synthase enzyme encoded by the isolated nucleic acid molecule of any of (1) through (12) above by one to three conservative amino acid substitutions, wherein a conservative amino acid substitution is defined as one of the following substitutions: A→G or S; R→K; N→Q or H; D→E; C→S; Q→N; G→D; G→A or P; H→N or Q; I→L or V; L→I or V; K→R or Q or E; M→L or Y or I; F→M or L or Y; S→T; T→S; W→Y; Y→W or F; and V→I or L.

The present invention also encompasses an isolated nucleic acid molecule that is at least 95% identical to any of the isolated nucleic acid molecules described above that encodes a variant *S. cerevisiae* squalene synthase enzyme, such that the isolated nucleic acid molecule also encodes a variant *S. cerevisiae* squalene synthase enzyme that, when present and expressed in vivo in *Saccharomyces cerevisiae*, catalyzes the synthesis of squalene at a sufficiently high rate that supplementation of the *S. cerevisiae* with a sterol is not required and that has a reduced squalene synthase activity.

Also within the scope of the present invention is an isolated nucleic acid molecule that includes therein, as a discrete, continuous nucleic acid segment, the isolated nucleic acid molecule encoding the variant squalene synthase as described above. This embodiment of the invention can include, at either the 5'-terminus, the 3'-terminus, or both, additional nucleic acid sequences such as linkers, adaptors, restriction endonuclease cleavage sites, regulatory sequences such as promoters, enhancers, or operators, or coding sequences, to which the discrete, continuous nucleic acid segment is operatively linked.

Also within the scope of the present invention are vectors including therein nucleic acid segments according to the present invention as described above, as well as host cells transformed or transfected with the vectors or host cells including therein a nucleic acid segment encoding the variant squalene synthase enzyme according to the present invention, as described above.

The present invention further includes a variant squalene synthase enzyme encoded by a nucleic acid sequence according to the present invention as described above. The variant squalene synthase enzyme can be, but is not limited to a variant *S. cerevisiae* squalene synthase enzyme. Variant *S. cerevisiae* squalene synthase enzymes according to the present invention include, but are not limited to, at least one of the mutants listed in Table 2.

Another aspect of the present invention includes a host cell containing and/or expressing a variant squalene synthase enzyme of the present invention as described above (a variant squalene synthase enzyme). The host cell, in this alternative, includes at least one copy of a nucleic acid sequence encoding the enzyme. The copy of the nucleic acid sequence encoding the enzyme can be present in the chromosome of a prokaryotic (bacterial) cell or in one chromosome of a eukaryotic cell.

Alternatively, the copy of the nucleic acid sequence encoding the enzyme can be present in a vector or plasmid that is present in the cell.

Another aspect of the invention is a method of isolating a defective ERG9 gene. In general, this method comprises the steps of:

(1) isolating a wild-type ERG9 gene to produce an isolated wild-type ERG9 gene;

(2) subjecting the isolated wild-type ERG9 gene to mutagenesis to generate a pool of erg9 mutants;

(3) transforming mutants from the pool of erg9 mutants generated in step (2) into a strain of a eukaryotic microbial host that contains a plasmid expressing a terpene synthase gene that produces a detectable and measurable terpene product, the strain of the eukaryotic microbial host being transformed in such a manner that replacement of the preexisting ERG9 allele with an erg9 mutation allows the strain to grow in a sterol-free medium; and (4) isolating a transformant from step (3) that produces a level of terpene product at least equivalent to the level of terpene product produced by a strain of the eukaryotic microbial host expressing the terpene synthase gene that requires a sterol in the medium for growth.

Another aspect of the present invention is a method of isolating a variant squalene synthase enzyme. The variant squalene synthase enzyme to be isolated by the methods of the invention is as described above.

In general, this method comprises the steps of:

(a) culturing a host cell that expresses a variant squalene synthase gene according to the present invention or that contains a variant squalene synthase enzyme according to the present invention; and (b) isolating the variant squalene synthase enzyme from the host cell.

Yet another aspect of the present invention is a method of producing an isoprenoid using a host cell containing a mutated ERG9 gene, which defective ERG9 gene encodes a variant squalene synthase enzyme.

In one alternative, a host cell that includes a mutated ERG9 gene encoding a variant squalene synthase enzyme further includes at least one isoprenoid synthase gene, so that the farnesyl pyrophosphate produced in the host cell, which is available in greater concentrations for isoprenoid biosynthesis can be converted to an isoprenoid by the isoprenoid synthase encoded by the isoprenoid synthase gene.

This alternative, in general, comprises the steps of:

(1) providing a host cell that includes a mutated ERG9 gene that encodes a variant squalene synthase enzyme according to the present invention and at least one isoprenoid synthase gene;

(2) allowing the host cell to produce farnesyl pyrophosphate and to synthesize the isoprenoid from the farnesyl pyrophosphate; and (3) isolating the isoprenoid synthesized by the host cell.

In another alternative method for producing an isoprenoid, the method, in general, comprises the steps of:

(1) providing a host cell that includes a mutated ERG9 gene that encodes a variant synthase enzyme according to the present invention;

(2) allowing the host cell to produce farnesyl pyrophosphate;

(3) isolating farnesyl pyrophosphate from the host cell;

(4) reacting the farnesyl pyrophosphate in vitro with one or more isoprenoid synthases to synthesize the isoprenoid; and (5) isolating the isoprenoid.

BRIEF DESCRIPTION OF THE DRAWINGS

These and other features, aspects, and advantages of the present invention will become better understood with regard to the following description, appended claims, and accompanying drawings.

FIGS. 2A-2D depict the sequences of the wild-type ERG9 gene including sequences 245 base pairs upstream of the start site (SEQ ID NO: 3). In FIGS. 2A-2D, the underlined nucleotides shown at the 5'-terminus and 3'-terminus of the ERG9 gene sequence represent the upstream primer (7-162.1) 5'-CCATCTTCAACAACAATACCG-3' (SEQ ID NO: 1) and the downstream primer (7-162.2) 5'-GTACTTAGTTATTGT-TCGG-3' (SEQ ID NO: 2).

DETAILED DESCRIPTION OF THE INVENTION

Definitions

Figure 1:
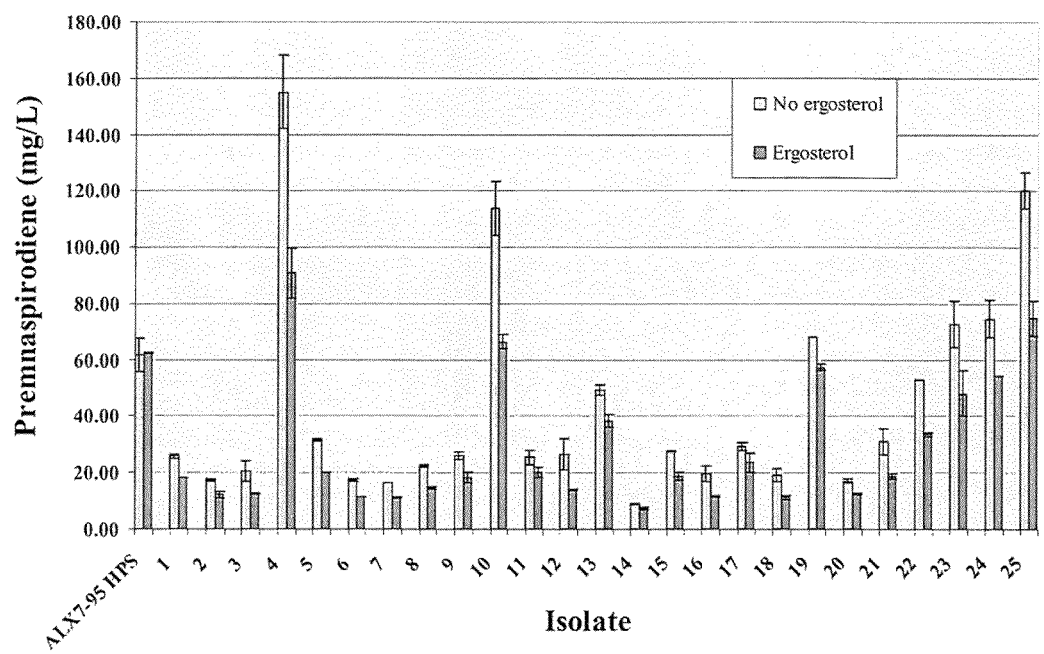
FIG. 1 depicts a graph showing the concentration of premnaspirodiene in mg/L for each of the 25 isolates grown with and without ergosterol supplementation.

As used herein, the term "nucleic acid," "nucleic acid sequence," "polynucleotide," or similar terms, refers to a deoxyribonucleotide or ribonucleotide oligonucleotide or polynucleotide, including single- or double-stranded forms, and coding or non-coding (e.g., "antisense") forms. The term encompasses nucleic acids containing known analogues of natural nucleotides. The term also encompasses nucleic acids including modified or substituted bases as long as the modified or substituted bases interfere neither with the Watson-Crick binding of complementary nucleotides or with the binding of the nucleotide sequence by proteins that bind specifically. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs). (Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan, J. Med. Chem. 36:1923-1937 (1993); Antisense Research and Applications (1993, CRC Press). PNAs contain non-ionic backbones, such as N-(2-aminoethyl)glycine units. Phosphorothioate linkages are described in, e.g. U.S. Pat. Nos. 6,031,092; 6,001,982; 5,684,148; WO 97/03211; WO 96/39154; Mata, Toxicol. Appl. Pharmacol. 144:189-197 (1997). Other synthetic backbones encompassed by the term include methylphosphonate linkages or alternating methylphosphonate and phosphodiester linkages (U.S. Pat. No. 5,962,674; Strauss-Soukup, Biochemistry 36:8692-8698 (1997)), and benzylphosphonate linkages (U.S. Pat. No. 5,532,226; Samstag, Antisense Nucleic Acid Drug Dev 6:153-156 (1996)). Bases included in nucleic acids include any of the known base analogs of DNA and RNA including, but not limited to, 4-acetyl cytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethyl-aminomethyluracil, dihydrouracil, inosine, $N^6$-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, N⁶-methyladenine, 7-methylguanine, 5-methylaminomethyluracil, 5-methoxy-amino-methyl-2-thiouracil, β-D-mannosylqueosine, 5'-methoxycarbonylmethyluracil, 5-methoxyuracil, 2-methylthio-N⁶-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. DNA may be in the form of cDNA, in vitro polymerized DNA, plasmid DNA, parts of a plasmid DNA, genetic material derived from a virus, linear DNA, vectors (e.g. P1, PAC, BAC, YAC, and artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. Additionally, the terms "nucleic acid" or "nucleic acid molecule" refer to a deoxyribonucleotide or ribonucleotide polymer in either single- or double-stranded form, and unless otherwise limited, would encompass known analogs of natural nucleotides that can function in a similar manner as naturally occurring nucleotides. A "nucleotide sequence" also refers to a polynucleotide molecule or oligonucleotide molecule in the form of a separate fragment or as a component of a larger nucleic acid. The nucleotide sequence or molecule may also be referred to as a "nucleotide probe." Some of the nucleic acid molecules of the invention are derived from DNA or RNA isolated at least once in substantially pure form and in a quantity or concentration enabling identification, manipulation, and recovery of its component nucleotide sequence by standard biochemical methods. Examples of such methods, including methods for PCR protocols that may be used herein, are disclosed in Sambrook et al., Molecular Cloning: A Laboratory Manual, 2nd ed., Cold Spring Harbor Laboratory Press, New York (1989), Ausubel, F. A., et al., eds., Current Protocols in Molecular Biology, John Wiley and Sons, Inc., New York (1987), and Innis, M., et al. (Eds.) PCR Protocols: A Guide to Methods and Applications, Academic Press, San Diego, Calif. (1990). Reference to a nucleic acid molecule also includes its complement as determined by the standard Watson-Crick base-pairing rules, with uracil (U) in RNA replacing thymine (T) in DNA where necessary, unless the complement is specifically excluded.

As described herein, the nucleic acid molecules of the invention include DNA in both single-stranded and double-stranded form, as well as the DNA or RNA complement thereof. DNA includes, for example, DNA, genomic DNA, chemically synthesized DNA, DNA amplified by PCR, and combinations thereof. Genomic DNA, including translated, non-translated and control regions, may be isolated by conventional techniques, e.g., using any one of the cDNAs of the invention, or suitable fragments thereof, as a probe, to identify a piece of genomic DNA which can then be cloned using methods commonly known in the art.

Polypeptides encoded by the nucleic acids of the invention are encompassed by the invention. As used herein, reference to a nucleic acid "encoding" a protein or polypeptide encompasses not only cDNAs and other intronless nucleic acids, but also DNAs, such as genomic DNA, with introns, on the assumption that the introns included have appropriate splice donor and acceptor sites that will ensure that the introns are spliced out of the corresponding transcript when the transcript is processed in a eukaryotic cell. Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. Exemplary methods of making such alterations are disclosed by Walder et al., Gene, 42:133 (1986); Bauer et al., Gene 37:73 (1985); Craik, BioTechniques, Jan. 12-19 (1985); Smith et al., Genetic Engineering Principles and Methods, Plenum Press, (1981); Kunkel (PNAS USA 82:488 (1985); Kunkel et al., Methods in Enzymol. 154.367 (1987). The present invention thus encompasses any nucleic acid capable of encoding a protein of the current invention.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. Watson et al., Molecular Biology of the Gene, 4th Edition, 1987, Benjamin/Cummings, p. 224). In particular, such a conservative variant has a modified amino acid sequence, such that the change(s) do not substantially alter the proteins structure and/or activity, e.g., antibody activity, enzymatic activity, or receptor activity. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Len or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (I or Ile), leucine (L or Leu), methionine (M or Met), valine (V or Val); and (6) phenylalanine (F or Phe), tyrosine (Y or Tyr), tryptophan (W or Trp); (Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations" when the three-dimensional structure and the function of the protein to be delivered are conserved by such a variation.

As used herein, the term "isolated" with reference to a nucleic acid molecule or polypeptide or other biomolecule means that the nucleic acid or polypeptide has been separated from the natural environment from which the polypeptide or nucleic acid were obtained. It may also mean that the biomolecule has been altered from the natural state. For example, a polynucleotide or a polypeptide naturally present in a living animal is not "isolated," but the same polynucleotide or polypeptide separated from the coexisting materials of its natural state is "isolated," as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith et al., Gene 67:3140 (1998). The terms "isolated" and "purified" are sometimes used interchangeably.

Thus, by "isolated" it is meant that the nucleic acid is free of the coding sequences of those genes that, in a naturally-occurring genome, immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

"Isolated" or "purified" also refer to preparations made from biological cells or hosts and means any cell extract containing the indicated DNA or protein including a crude extract of the DNA or protein of interest. For example, in the case of a protein, a purified preparation can be obtained following an individual technique or a series of preparative or biochemical techniques and the protein of interest can be present at various degrees of purity in these preparations. Particularly for proteins, the procedures may include for example, but are not limited to, ammonium sulfate fractionation, gel filtration, ion exchange chromatography, affinity chromatography, density gradient centrifugation, electrofocusing, chromatofocusing, and electrophoresis. As used herein, the term "substantially purified," when applied to a composition or extract derived from yeast, and wherein the composition or extract contains an isoprenoid, is hereby defined as containing at least about twice the concentration of isoprenoid in proportion to yeast material, wherein yeast material is defined as being selected from the group consisting of yeast cell membrane, yeast organelle, yeast cytoplasm, yeast microsomal fraction, yeast cell, and yeast extract.

A preparation of DNA or protein that is "substantially pure" or "isolated" refers to a preparation free from naturally occurring materials with which such DNA or protein is normally associated in nature. "Essentially pure" means a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" includes culture media, for example, spent culture media from which the cells have been removed.

A "vector" is a nucleic acid that is capable of transporting another nucleic acid. Vectors may be, for example, plasmids, viruses, cosmids or phage. An "expression vector" is a vector that is capable of directing expression of a protein encoded by one or more genes carried by the vector when it is present in the appropriate environment. Examples of vectors are those that can autonomously replicate and express structural gene products present in the DNA segments to which they are operatively linked. Vectors, therefore, can contain the replicons and selectable markers described earlier. Vectors include, but are not necessarily limited to, expression vectors.

As used herein with regard to nucleic acid molecules, including DNA fragments, the phrase "operatively linked" means the sequences or segments have been covalently joined, preferably by conventional phosphodiester bonds, into one strand of DNA, whether in single or double-stranded form such that operatively linked portions function as intended.

As used herein, the phrase "substantially identical" means that a relevant sequence is at least 70%, 75%, 80%, 85%, 90%, 92%, 95%, 96%, 97%, 98%, or 99% identical to a given sequence. By way of example, such sequences may be allelic variants, sequences derived from various species, or they may be derived from the given sequence by truncation, deletion, amino acid substitution or addition. Percent identity between two sequences is determined by standard alignment algorithms such as ClustalX when the two sequences are in best alignment according to the alignment algorithm.

In order to maximize production of farnesyl pyrophosphate (FPP), novel mutants in the ERG9 gene of *Saccharomyces cerevisiae* have been developed. The ERG9 gene is the gene encoding squalene synthase. These mutants have reduced, but not eliminated, squalene synthase activity. As such, they allow sufficient production of squalene and subsequent sterols to allow growth, but are sufficiently reduced in activity to allow accumulation of FPP and overproduction of terpenes. This is done, unlike in previous approaches, by generating and utilizing defective squalene synthase genes, Which when expressed result in reduced cellular squalene synthase, activity rather than downregulating the transcription of a normally active squalene synthase enzyme. This makes the reduced squalene synthase activity independent of the activity of a repressor.

Accordingly, one aspect of the present invention is an isolated nucleic acid molecule that encodes a squalene synthase enzyme that, when present and expressed in vivo in a eukaryotic microbial host cell, catalyzes the synthesis of squalene at a sufficiently high rate that supplementation of the eukaryotic microbial host cell with a sterol is not required and that has a reduced squalene synthase activity (referred to herein for convenience as a variant squalene synthase enzyme). Typically, the variant squalene synthase enzyme encoded by the isolated nucleic acid molecule of the present invention has a reduced $V_{max}$ for squalene synthesis. $V_{max}$ is the maximum rate of a reaction being catalysed by an enzyme. Alternatively, the variant squalene synthase enzyme encoded by the isolated nucleic acid molecule of the present invention has an increased Michaelis constant ($K_m$) for its FPP substrate, in which case the enzyme is less active at a given intracellular concentration of FPP than the wild-type enzyme. The $K_m$ is a means of characterising an enzyme's affinity for a substrate. The $K_m$ in an enzymatic reaction is the substrate concentration at which the reaction rate is half its maximum speed. Typically, the squalene synthase enzyme encoded by the isolated nucleic acid molecule of the present invention, when expressed in vivo in the eukaryotic microbial host cell, produces squalene at a rate of less than 75% of the wild-type enzyme. Preferably, the squalene synthase enzyme encoded by the isolated nucleic acid molecule of the present invention, when expressed in vivo in the eukaryotic microbial host cell, produces squalene at a rate of less than 50% of the wild-type enzyme. More preferably, the squalene synthase enzyme encoded by the isolated nucleic acid molecule of the present invention, when expressed in vivo in the eukaryotic microbial host cell, produces squalene at a rate of less than 25% of the wild-type enzyme. The eukaryotic microbial host cell is typically, but is not limited to, a fungal host cell. The fungal host cell is typically, but is not limited to, a yeast host cell, such as a *Saccharomyces cerevisiae* host cell or other host cells of the genus *Saccharomyces*. Similarly, the variant squalene synthase is not limited to a squalene synthase of *Saccharomyces cerevisiae*, but can be a squalene synthase of another species of *Saccharomyces* or a squalene synthase of any organism that has a gene that catalyzes the conversion of farnesyl pyrophosphate into squalene.

Isolated nucleic acid molecules according to the present invention include, but are not limited to, the following isolated nucleic acid molecules:

(1) an isolated nucleic acid molecule encoding a variant *S. cerevisiae* squalene synthase enzyme as shown as Mutant 4 in Table 2 of the present invention;

(2) an isolated nucleic acid molecule encoding a mutated *S. cerevisiae* squalene synthase enzyme as shown as Mutant 10 in Table 2 of the present invention;

(3) an isolated nucleic acid molecule encoding a mutated *S. cerevisiae* squalene synthase enzyme as shown as Mutant 14 in Table 2 of the present invention;

(4) an isolated nucleic acid molecule encoding a mutated *S. cerevisiae* squalene synthase enzyme as shown as Mutant 19 in Table 2 of the present invention;

(5) an isolated nucleic acid molecule encoding a mutated *S. cerevisiae* squalene synthase enzyme as shown as Mutant 22 in Table 2 of the present invention;

(6) an isolated nucleic acid molecule encoding a mutated *S. cerevisiae* squalene synthase enzyme as shown as Mutant 23 in Table 2 of the present invention;

(7) an isolated nucleic acid molecule encoding a mutated *S. cerevisiae* squalene synthase enzyme as shown as Mutant 24 in Table 2 of the present invention;

(8) an isolated nucleic acid molecule encoding a mutated *S. cerevisiae* squalene synthase enzyme as shown as Mutant 25 in Table 2 of the present invention;

(9) an isolated nucleic acid molecule encoding a mutated *S. cerevisiae* squalene synthase enzyme as shown as Mutant 69 in Table 2 of the present invention;

(10) an isolated nucleic acid molecule identical to any of (3), (4), (6), (7), or (8), above, except that one or more of the silent mutations in nucleic acid molecules (3), (4), (6), (7), or (8) are omitted;

(11) an isolated nucleic acid molecule encoding a variant *S. cerevisiae* squalene synthase protein in which the wild-type *S. cerevisiae* squalene synthase enzyme is mutated with the same amino acid changes as in any of (1) through (10) above;

(12) an isolated nucleic acid encoding a squalene synthase protein containing any of the amino acid changes in any of (1) through (10). Although some of the mutations described above are designated as "silent," meaning that they do not affect the amino acid inserted into the polypeptide chain at that position, there is evidence that such mutations may affect protein function in a number of ways, including altering folding patterns due to effects on translation due to codon The invention includes an isolated nucleic acid molecule encoding a squalene synthase enzyme that differs from the squalene synthase enzyme encoded by the nucleic acid molecule in any of (1) through (11), above, by one to three conservative amino acid substitutions, in which a conservative amino acid substitution is defined as one of the following substitutions: A→G or S; R→K; N→Q or H; D→E; C→S; Q→N; G→D; G→A or P; H→N or Q; I→L or V; L→I or V; K→R or Q or E; M→L or Y or I; F→M or L or Y; S→T; T→S; W→Y; Y→W or F; and V→I or L. Preferably, the isolated nucleic acid molecule encodes a squalene synthase protein that differs from the squalene synthase protein encoded by the nucleic acid molecule in any of (1) through (10) by one or two conservative amino acid substitutions. More preferably, the isolated nucleic acid molecule encodes a squalene synthase protein that differs from the squalene synthase protein encoded by the nucleic acid molecule in any of (1) through (11) by one conservative amino acid substitution.

The invention includes an isolated nucleic acid molecule that is at least 95% identical to any of the isolated nucleic acid molecules described above that encodes a mutated *S. cerevisiae* squalene synthase enzyme, such that the isolated nucleic acid molecule also encodes a mutated *S. cerevisiae* squalene synthase enzyme that, when present and expressed in vivo in *Saccharomyces cerevisiae*, catalyzes the synthesis of squalene at a sufficiently high rate that supplementation of the *S. cerevisiae* with sterols is not required and that has a reduced squalene synthase activity. Typically, the isolated nucleic acid molecule is at least 97.5% identical to any of the isolated nucleic acid molecules described above. Preferably, the isolated nucleic acid molecule is at least 99% identical to any of the isolated nucleic acid molecules described above. More preferably, the isolated nucleic acid molecule is at least 99.5% identical to any of the isolated nucleic acid molecules described above. Most preferably, the isolated nucleic acid molecule is at least 99.8% identical to any of the isolated nucleic acid molecules described above. For these purposes, "identity" is defined according to the Needleman-Wunsch algorithm (S. B. Needleman & C. D. Wunsch, "A General Method Applicable to the Search for Similarities in the Amino Acid Sequence of Two Proteins," J. Mol. Biol. 48: 443-453 (1970)).

Nucleic acid molecules according to the present invention and having the desired degree of identity are not limited to nucleic acid molecules derived from *S. cerevisiae*; they include nucleic acid molecules derived from other species of *Saccharomyces*, or, as described above, derived from any organism that has a gene capable of catalyzing the conversion of farnesyl pyrophosphate into squalene.

Additionally, isolated nucleic acid molecules according to the present invention further include isolated nucleic acid molecules, which encode a squalene synthase enzyme, and when expressed in a eukaryotic microbial host in which no other squalene synthase enzyme is expressed, result in a significant reduction of conversion of farnesyl pyrophosphate to squalene as described above. In one alternative, a nucleic acid molecule according to the present invention, when expressed in vivo, causes a host cell to produce a greater concentration of an isoprenoid in grams of isoprenoid per liter of culture than a corresponding host cell expressing a wild-type nucleic acid molecule. These isolated nucleic acid molecules have at least one change from a nucleic acid molecule that includes the coding region for the wild-type ERG9 gene and its flanking sequences, including the sequences both upstream and downstream from the coding region. This at least one change reduces the squalene synthase activity, even though the specific activity may potentially be unaltered. The reduction of the activity of the squalene synthase enzyme can occur through one or more of the following mechanisms: (1) reduction in transcription so that less mRNA that can be translated into squalene synthase enzyme is generated; (2) reduction of mRNA stability, again reducing translation; and (3) reduction of enzyme stability brought about by an increased rate of protein degeneration in vivo. In other words, either: (1) the specific activity of the resulting squalene synthase enzyme is reduced through at least one change in the amino acid sequence of the enzyme expressed from the nucleic acid molecule; or (2) the in vivo activity of the enzyme is reduced through a reduction in transcription, a reduction in translation, or a reduction of enzyme stability.

The nucleic acid described above can be DNA, RNA, or a RNA-DNA hybrid, but is typically DNA. The nucleic acid described above can be single-stranded or double-stranded. If the nucleic acid is single-stranded, either the strand described or its complement can be the coding strand and is within the scope of the invention.

Also within the scope of the invention is an isolated nucleic acid molecule that includes therein, as a discrete, continuous nucleic acid segment, the isolated nucleic acid molecule encoding the variant squalene synthase. This embodiment of the invention can include, at either the 5'-terminus, the 3'-terminus, or both, additional nucleic acid sequences such as linkers, adaptors, restriction endonuclease cleavage sites, regulatory sequences such as promoters, enhancers, or operators, or coding sequences, to which the discrete, continuous nucleic acid segment is operatively linked. In the event that the isolated nucleic acid molecule includes additional coding sequences, the isolated nucleic acid molecule can encode a fusion protein having *S. cerevisiae* squalene synthase activity.

Also within the scope of the invention are vectors including therein nucleic acid segments according to the present invention as described above. The vectors can be capable of replication in prokaryotes (bacteria) or in eukaryotes (yeast or cells of higher organisms). In one alternative, the vectors are capable of replication in yeast, for example, *S. cerevisiae*. In yeast, a number of vectors containing constitutive or inducible promoters may be used. For a review, see Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH1 or LEU2 or an inducible promoter such as GAL4 may be used (Cloning in Yeast, Ch. 3, Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

Appropriate cloning and expression vectors for use with bacterial, fungal, yeast, and mammalian cellular hosts are described, for example, in Pouwels et al., Cloning Vectors. A Laboratory Manual, Elsevier, N.Y., (1985). Cell-free translation systems could also be employed to produce the disclosed polypeptides using RNAs derived from DNA constructs disclosed herein.

Examples of expression vectors that can be used in prokaryotic host cells include those derived from commercially available plasmids such as the cloning vector pET plasmids (Novagen, Madison, Wis., USA) or pBR322 (ATCC 37017). The pBR322 vector contains genes for ampicillin and tetracycline resistance and thus provides simple means for identifying transformed cells. To construct an expression vector using pBR322, an appropriate promoter and a DNA sequence encoding one or more of the polypeptides of the invention are inserted into the pBR322 vector. Other commercially available vectors include, for example, pKK223-3 (Pharmacia Fine Chemicals, Uppsala, Sweden) and pGEM-1 (Promega Biotec, Madison, Wis., USA). Other commercially available vectors include those that are specifically designed for the expression of proteins; these would include pMAL-p2 and pMAL-c2 vectors that are used for the expression of proteins fused to maltose binding protein (New England Biolabs, Beverly, Mass., USA).

Promoter sequences commonly used for recombinant prokaryotic host cell expression vectors include the bacteriophage T7 promoter (Studier and Moffatt, J. Mol. Biol. 189:113 (1986)), β-lactamase (penicillinase), lactose promoter system (Chang et al., Nature 275:615, 1978; Goeddel et al., Nature 281:544 (1979)), tryptophan (trp) promoter system (Goeddel et al., Nucl. Acids Res. 8:4057 (1980); EP-A-36776), and tac promoter (Maniatis, Molecular Cloning: A Laboratory Manual, Cold Spring Harbor Laboratory, p. 412 (1982)). A particularly useful prokaryotic host cell expression system employs a phage λ PL promoter and a cI857ts thermolabile repressor sequence. Plasmid vectors available from the American Type Culture Collection (ATCC), which incorporate derivatives of the $P_L$ promoter, include plasmid pHUB2 (resident in *E. coli* strain JMB9 (ATCC 37092)) and pPLc28 (resident in *E. coli* RR1 (ATCC 53082)).

As detailed below, nucleic acid segments according to the present invention can also be incorporated in vectors suitable for introduction into yeast cells, such as, for example, *Saccharomyces* (particularly *S. cerevisiae*), *Pichia* (particularly *P. pastoris*), and *Kluyveromyces* (particularly *K. lactis*). Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, 1980), or other glycolytic enzymes (Hess et al., Adv. Enzyme Reg. 7:149 (1969); Holland et al., Biochem. 17:4900, (1978)), such as enolase, glyceraldehyde phosphate dehydrogenase, hexokinase, pyruvate decarboxylase, phosphofruktokinase, glucose phosphate isomerase, 3-phosphoglycerate mutase, pyruvate kinase, triosephosphate isomerase, phosphoglucose isomerase, and glucokinase. Other suitable vectors and promoters for use in yeast expression are described in Hitzeman, EPA-73,657 or in Fleer et al., Gene, 107:285-295 (1991); and van den Berg et al., Bio/Technology, 8:135-139 (1990). Another alternative is the glucose-repressible ADH2 promoter described by Russell et al. (J. Biol. Chem. 258:2674, (1982)) and Beier et al. (Nature 300:724 (1982)). Shuttle vectors replicable in both yeast and *E. coli* can be constructed by inserting DNA sequences from pBR322 for selection and replication in *E. coli* ($Amp^r$ gene and origin of replication) into the above-described yeast vectors.

When the vectors are capable of replication in cells of higher organisms, the higher organisms can be plants or animals, including mammals. In cases where plant expression vectors are used, the expression of a mutated *S. cerevisiae* squalene synthase coding sequence according to the present invention may be driven by any of a number of promoters. For example, viral promoters such as the 35S RNA and 19S RNA promoters of CaMV (Brisson et al., Nature, 310:511-514 (1984)), or the coat protein promoter to TMV (Takamatsu et al., EMBO J., 6:307-311 (1987)) may be used; alternatively, plant promoters such as the small subunit of RUBISCO (Coruzzi et al., EMBO J. 3:1671-1680 (1984); Broglie et al., Science 224:838-843 (1984)); or heat shock promoters, e.g., soybean hsp17.5-E or hsp17.3-B (Gurley et al., Mol. Cell. Biol., 6:559-565 (1986)) may be used. These constructs can be introduced into plant cells using Ti plasmids, Ri plasmids, plant virus vectors, direct DNA transformation, microinjection, electroporation, or other techniques that are well known in the art. For reviews of such techniques see, for example, Weissbach and Weissbach, Methods for Plant Molecular Biology, Academic Press, NY, Section VIII, pp. 421-463 (1988); and Grierson and Corey, Plant Molecular Biology, 2d Ed., Blackie, London, Ch. 7-9 (1988). Eukaryotic cells are alternative host cells for the expression of mutated *S. cerevisiae* squalene synthase coding sequences. Such host cell lines may include but are not limited to CHO, VERO, BHK, HeLa, COS, MDCK, 293, and W138.

Mammalian cell systems that utilize recombinant viruses or viral elements to direct expression may be engineered. For example, when using adenovirus expression vectors, the coding sequence of a variant squalene synthase enzyme may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the variant squalene synthase enzyme in infected hosts (Logan and Shenk, PNAS USA 81:3655-3659 (1984)). Alternatively, the vaccinia virus 7.5K promoter may be used. (Mackett et al., PNAS USA, 79:7415-7419 (1982); Mackett et al., J. Virol. 49:857-864 (1984); Panicali, et al., PNAS USA, 79:4927-4931 (1982)). Of particular interest are vectors based on bovine papilloma virus which have the ability to replicate as extrachromosomal elements (Sarver et al., Mol. Cell. Biol. 1:486 (1981)). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the variant squalene synthase enzyme in host cells (Cone and Mulligan, PNAS USA 81:6349-6353 (1984)). High level expression may also be achieved using inducible promoters, including, but not limited to, the metallothionein IIA promoter and heat shock promoters.

Also within the scope of the invention are host cells including a nucleic acid segment encoding the variant squalene synthase according to the present invention, as described above. These host cells are typically transformed or transfected with the nucleic acid segment; methods for such transformation or transfection are described above. The term "nucleic acid segment" is used herein to include the following alternatives: (1) a vector including therein the variant squalene synthase; or (2) a chromosome of the host cell including therein the variant squalene synthase. The vector or chromosome can include, as described above, nucleic acid sequences either 5'-, 3'-, or both 5'- and 3'- to the coding sequence of the mutated *S. cerevisiae* squalene synthase, such as, but not limited to, linkers, adaptors, restriction endonuclease cleavage sites, regulatory sequences such as promoters, enhancers, or operators, or coding sequences. The host cells can be prokaryotic cells, such as bacteria, or can be eukaryotic cells, such as yeast cells, plant cells, or animal cells. If the host cells are yeast cells, they are typically *S. cerevisiae*, although other genera of yeast, such as *Pichia* (*Pichia pastoris*) or *Kluyveromyces* (*Kluyveromyces lactis*) can also be employed. If the cells are plant cells, many types of plant cells are suitable host cells; one frequently employed host cell is *Arabidopsis thaliana*. If the cells are animal cells, they can be insect cells or mammalian cells.

In host cells according to the present invention including therein a nucleic acid segment encoding the variant squalene synthase as described above, the nucleic acid segment can be incorporated into a vector as described above. Alternatively, the nucleic acid segment can be integrated into a chromosome of the host cell. Methods for integrating the nucleic acid segment encoding the variant squalene synthase as described above into the chromosome of a prokaryotic cell (i.e., a bacterium) or into one chromosome of a eukaryotic cell are known in the art. As described above, in this application, the nucleic acid is typically DNA.

DNA sequences encoding variant squalene synthase can be obtained by several methods. For example, the DNA can be isolated using hybridization procedures that are well known in the art. These include, but are not limited to: (1) hybridization of probes to genomic or cDNA libraries to detect shared nucleotide sequences; (2) antibody screening of expression libraries to detect shared structural features; and (3) synthesis by the polymerase chain reaction (PCR). RNA sequences of the invention can be obtained by methods known in the art (See, for example, Current Protocols in Molecular Biology, Ausubel, et al., Eds. (1989)).

The development of specific DNA sequences encoding variant squalene synthases of the invention can be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA is the least common. This is especially true when it is desirable to obtain the microbial expression of eukaryotic polypeptides, such as yeast polypeptides, due to the presence of introns. For obtaining nucleic acid sequences encoding variant squalene synthases according to the present invention, the synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be clones. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., Nucleic Acid Research 11:2325 (1983)).

Nucleotide sequences encompassed by the present invention can also be incorporated into a vector as described above, including, but not limited to, an expression vector, and used to transfect or transform suitable host cells, as is well known in the art. The vectors incorporating the nucleotide sequences that are encompassed by the present invention are also within the scope of the invention. Host cells that are transformed or transfected with the vector or with polynucleotides or nucleotide sequences of the present invention are also within the scope of the invention. The host cells can be prokaryotic or eukaryotic; if eukaryotic, the host cells can be mammalian cells, insect cells, or yeast cells. If prokaryotic, the host cells are typically bacterial cells.

Transformation of a host cell with recombinant DNA may be carried out by conventional techniques as are well known to those skilled in the art. Where the host is prokaryotic, such as *Escherichia coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used.

A variety of host-expression vector systems may be utilized to express the nucleic acid sequence encoding the variant squalene synthase enzymes of the present invention. These include but are not limited to microorganisms such as bacteria transformed with recombinant bacteriophage DNA, plasmid DNA or cosmid DNA expression vectors containing a variant squalene synthase enzyme coding sequence; yeast transformed with recombinant yeast expression vectors containing the variant squalene synthase enzyme coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a variant squalene synthase enzyme coding sequence; insect cell systems infected with recombinant virus expression vectors (e.g., baculovirus) containing a variant squalene synthase enzyme coding sequence; or animal cell systems infected with recombinant virus expression vectors (e.g., retroviruses, adenovirus, vaccinia virus) containing a variant squalene synthase enzyme coding sequence, or transformed animal cell systems engineered for stable expression. In such cases where glycosylation may be important, expression systems that provide for translational and post-translational modifications may be used; e.g., mammalian, insect, yeast or plant expression systems.

Depending on the host/vector system utilized, any of a number of suitable transcription and translation elements, for example, constitutive and inducible promoters, transcription enhancer elements, transcription terminators, may be used in the expression vector (Bitter et al., Methods in Enzymology, 153:516-544 (1987)). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted variant squalene synthase enzyme coding sequence.

In bacterial systems a number of expression vectors may be advantageously selected depending upon the use intended for the variant squalene synthase enzyme expressed, and whether it is desired to isolate the enzyme and in what state of purity. For example, when large quantities are to be produced, vectors which direct the expression of high levels of fusion protein products that are readily purified may be desirable. Those which are engineered to contain a cleavage site to aid in recovering the protein are preferred. Such vectors include, but are not limited to, the *Escherichia coli* expression vector pUR278 (Ruther et al., EMBO J., 2:1791 (1983)), in which the valiant squalene synthase enzyme coding sequence may be ligated into the vector in frame with the lac Z coding region so that a hybrid variant squalene synthase enzyme-lac Z protein is produced as well as pIN vectors (Inouye and Inouye, Nucleic Acids Res. 13:3101-3109 (1985); Van Heeke and Schuster, J. Biol. Chem. 264:5503-5509 (1989)).

In yeast, a number of vectors containing constitutive or inducible promoters may be used. For a review, see Current Protocols in Molecular Biology, Vol. 2, Ed. Ausubel, et al., Greene Publish. Assoc. & Wiley Interscience, Ch. 13 (1988); Bitter et al., Expression and Secretion Vectors for Yeast, in Methods in Enzymology, Eds. Wu & Grossman, 31987, Acad. Press, N.Y., Vol. 153, pp. 516-544 (1987); Glover, DNA Cloning, Vol. II, IRL Press, Wash., D.C., Ch. 3 (1986); Bitter, Heterologous Gene Expression in Yeast, Methods in Enzymology, Eds. Berger & Kimmel, Acad. Press, N.Y., Vol. 152, pp. 673-684 (1987); and The Molecular Biology of the Yeast *Saccharomyces*, Eds. Strathern et al., Cold Spring Harbor Press. Vols. I and II (1982). A constitutive yeast promoter such as ADH1 or LEU2 or an inducible promoter such as GAL4 may be used (Cloning in Yeast, Ch. 3, R. Rothstein In: DNA Cloning Vol. 11, A Practical Approach, Ed. D M Glover, IRL Press, Wash., D.C. (1986)). Alternatively, vectors may be used which promote integration of foreign DNA sequences into the yeast chromosome.

In cases where plant expression vectors are used, the expression of a variant squalene synthase enzyme coding sequence may be driven by any of a number of promoters. For example, viral promoters such as the 35S RNA and 19S RNA promoters of CaMV (Brisson et al., Nature, 310:511-514 (1984)), or the coat protein promoter to TMV (Takamatsu et al., EMBO J., 6:307-311 (1987)) may be used; alternatively, plant promoters such as the small subunit of RUBISCO (Coruzzi et al., EMBO J. 3:1671-1680 (1984); Broglie et al., Science 224:838-843 (1984)); or heat shock promoters, e.g., soybean hsp17.5-E or hsp17.3-B (Gurley et al., Mol. Cell. Biol., 6:559-565 (1986)) may be used. These constructs can be introduced into plant cells using Ti plasmids, Ri plasmids, plant virus vectors, direct DNA transformation, microinjection, electroporation, or other techniques that are well known in the art. (Weissbach & Weissbach, Methods for Plant Molecular Biology, Academic Press, NY, Section VIII, pp. 421-463 (1988); Grierson and Corey, Plant Molecular Biology, 2d Ed., Blackie, London, Ch. 7-9 (1988).

An alternative expression system that can be used to express a variant squalene synthase enzyme of the present invention is an insect system. In one such system, *Autographa californica* nuclear polyhedrosis virus (AcNPV) is used as a vector to express foreign genes. The virus grows in *Spodoptera frugiperda* cells. The variant squalene synthase enzyme coding sequence may be cloned into non-essential regions (in *Spodoptera frugiperda*, for example, the polyhedrin gene) of the virus and placed under control of an AcNPV promoter (for example the polyhedrin promoter). Successful insertion of the variant squalene synthase enzyme coding sequence will result in inactivation of the polyhedrin gene and production of non-occluded recombinant virus (i.e., virus lacking the proteinaceous coat coded for by the polyhedrin gene). These recombinant viruses are then used to infect cells in which the inserted gene is expressed. (Smith et al., J. Virol. 46:584 (1983); U.S. Pat. No. 4,215,051).

Eukaryotic systems, and preferably mammalian expression systems, allow for proper post-translational modifications of expressed eukaryotic proteins to occur. Therefore, eukaryotic cells, such as mammalian cells that possess the cellular machinery for proper processing of the primary transcript, glycosylation, phosphorylation, and, advantageously secretion of the gene product, are the preferred host cells for the expression of a variant squalene synthase enzyme. Such host cell lines may include, for example CHO, VERO, BHK, HeLa, COS, MDCK, 293, and WI38. Other eukaryotic host cells are also suitable host cells for the expression of a variant squalene synthase enzyme or of nucleic acids according to the present invention, including, for example, microalgal cells.

Mammalian cell systems that utilize recombinant viruses or viral elements to direct expression may be engineered for use in the present invention. For example, when using adenovirus expression vectors, the coding sequence of a variant squalene synthase enzyme may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the variant squalene synthase enzyme in infected hosts (Logan and Shenk, PNAS USA 81:3655-3659 (1984)). Alternatively, the vaccinia virus 7.5K promoter may be used (Mackett et al., PNAS USA, 79:7415-7419 (1982); Mackett et al., J. Virol. 49:857-864, 1984; Panicali et al., (PNAS USA, 79:4927-4931 (1982)). Of particular interest are vectors based on bovine papilloma virus which have the ability to replicate as extrachromosomal elements (Sarver et al., Mol. Cell. Biol. 1:486 (1981)). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the variant squalene synthase enzyme in host cells (Cone and Mulligan, PNAS USA 81:6349-6353 (1984)). High level expression may also be achieved using inducible promoters, including, but not limited to, the metallothionein IIA promoter and heat shock promoters.

For long-term, high-yield production of recombinant proteins, stable expression is preferred. Rather than using expression vectors which contain viral origins of replication, host cells can be transformed with a cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in enriched media, and then are switched to a selective medium. A number of selection systems may be used, including but not limited to, the herpes simplex virus thymidine kinase (Wigler et al., Cell 11:223 (1977)), hypoxanthine-guanine phosphoribosyltransferase (Szybalska and Szybalski, PNAS USA, 48:2026 (1962)), and adenine phosphoribosyltransferase (Lowy et al., Cell, 22:817 (1980)) genes, which can be employed in tk⁻, hgprt⁻ or aprt⁻ cells, respectively. Additionally, antimetabolite resistance-conferring genes can be used as the basis of selection; for example, the genes for dhfr, which confer resistance to methotrexate (Wigler et al., Natl. Acad. Sci. USA, 77:3567 (1980); O'Hare et al., PNAS USA, 78:1527 (1981)); gpt, which confers resistance to mycophenolic acid (Mulligan and Berg, PNAS USA, 78:2072 (1981)); neo, which confers resistance to the aminoglycoside G418 (Colberre-Garapin et al., J. Mol. Biol., 150:1 (1981)); and hygro, which confers resistance to hygromycin (Santerre et al., Gene, 30:147 (1984)). Recently, additional selectable genes have been described, namely trpB, which allows cells to utilize indole in place of tryptophan; hisD, which allows cells to utilize histinol in place of histidine (Hartman and Mulligan, PNAS USA, 85:804 (1988)); and ODC (ornithine decarboxylase) which confers resistance to the ornithine decarboxylase inhibitor, 2-(difluoromethyl)-DL-ornithine, DFMO (McConlogue, In: Current Communications in Molecular Biology, Cold Spring Harbor Laboratory ed., (1987)).

Another aspect of the present invention is a variant squalene synthase enzyme encoded by a nucleic acid segment of the present invention as described above. These squalene synthase enzymes can be, for example, enzymes derived from *S. cerevisiae* or other species of the genus *Saccharomyces*; they can also include other squalene synthases derived from any organism that has a gene that catalyzes the conversion of farnesyl pyrophosphate into squalene.

When the variant squalene synthase enzymes are *S. cerevisiae* squalene synthase enzymes, they include, for example, the following:

(1) a variant *S. cerevisiae* squalene synthase enzyme as shown as Mutant 4 in Table 2;

(2) a variant *S. cerevisiae* squalene synthase enzyme as shown as Mutant 10 in Table 2;

(3) a variant *S. cerevisiae* squalene synthase enzyme as shown as Mutant 14 in Table 2;

(4) a variant *S. cerevisiae* squalene synthase enzyme as shown as Mutant 19 in Table 2;

(5) a variant *S. cerevisiae* squalene synthase enzyme as shown as Mutant 22 in Table 2;

(6) a variant *S. cerevisiae* squalene synthase enzyme as shown as Mutant 23 in Table 2;

(7) a variant *S. cerevisiae* squalene synthase enzyme as shown as Mutant 24 in Table 2;

(8) a variant *S. cerevisiae* squalene synthase enzyme as shown as Mutant 25 in Table 2;

(9) a variant *S. cerevisiae* squalene synthase enzyme as shown as Mutant 69 in Table 2;

(10) a variant *S. cerevisiae* squalene synthase enzyme in which the wild-type *S. cerevisiae* squalene synthase enzyme is mutated with the same amino acid changes as in any of (1) through (9) above;

(11) a variant *S. cerevisiae* squalene synthase enzyme containing any of the amino acid changes as in any of (1) through (10), above; and

(12) a variant *S. cerevisiae* squalene synthase enzyme in which the squalene synthase enzyme differs from the variant squalene synthase enzyme of any of (1) through (11) above by one to three conservative amino acid substitutions, wherein a conservative amino acid substitution is defined as one of the following substitutions: A→G or S; R→K; N→Q or H; D→E; C→S; Q→N; G→D; G→A or P; H→N or Q; I→L, or V; L→I or V; K→R or Q or E; M→L or Y or I; F→M or L or Y; S→T; T→S; W→Y; Y→W or F; and V→I or L.

Furthermore, with respect to these alternatives, typically, the variant squalene synthase enzyme has a reduced $V_{max}$ for squalene synthesis. Alternatively, the variant squalene synthase enzyme has an increased $K_m$ for its FPP substrate, in which case the enzyme is less active at a given intracellular concentration of FPP than the wild-type enzyme. Typically, the variant squalene synthase enzyme, when expressed in vivo in a suitable eukaryotic microbial host, as described above, produces squalene at a rate of less than 75% of the wild-type enzyme. Preferably, the variant squalene synthase enzyme, when expressed in vivo in a suitable eukaryotic microbial host, as described above, produces squalene at a rate of less than 50% of the wild-type enzyme. More preferably, the variant squalene synthase enzyme, when expressed in vivo in a suitable eukaryotic microbial host, produces squalene at a rate of less than 25% of the wild-type enzyme.

With respect to (12) of these alternatives, preferably, the variant *S. cerevisiae* squalene synthase enzyme differs from the variant *S. cerevisiae* squalene synthase enzyme of any of (1) through (10) above by one to two conservative amino acid substitutions. More preferably, the variant *S. cerevisiae* squalene synthase enzyme differs from the variant *S. cerevisiae* squalene synthase enzyme of any of (1) through (10) above by one conservative amino acid substitution.

Another aspect of the present invention is a host cell containing and/or expressing a variant squalene synthase enzyme of the present invention as described above. The host cell, in this alternative, includes at least one copy of a nucleic acid sequence encoding a variant squalene synthase enzyme. The at least one copy of the nucleic acid sequence encoding a variant squalene synthase enzyme can be present in the chromosome of a prokaryotic (bacterial) cell or in one chromosome of a eukaryotic cell. Alternatively, the at least one copy of the nucleic acid sequence encoding a variant squalene synthase enzyme can be present in a vector or plasmid that is present in the cell. The host cell, as described above, can be a prokaryotic or eukaryotic cell. If a prokaryotic cell, it can be a bacterial cell. If a eukaryotic cell, it can be a yeast cell, a plant cell, or an animal cell. Suitable host cells are described above.

Another aspect of the present invention is a method of isolating a mutated ERG9 gene. The mutated ERG9 gene is typically a *S. cerevisiae* gene, but can be a homologous gene from another species as described above.

In general, a method of isolating a mutated ERG9 gene according to the present invention comprises the steps of:

(1) isolating a wild-type ERG9 gene to produce an isolated wild-type ERG9 gene;

(2) subjecting the isolated wild-type ERG9 gene to mutagenesis to generate a pool of ERG9 erg9 mutants;

(3) transforming mutants from the pool of erg9 mutants generated in step (b) into a strain of a eukaryotic microbial host that contains a plasmid expressing a terpene synthase gene that produces a detectable and measurable terpene product, the strain of the eukaryotic microbial host being transformed in such a manner that replacement of the preexisting ERG9 allele with an erg9 mutation allows the strain to grow in a sterol-free medium; and (4) isolating a transformant from step (c) that produces a level of terpene product at least equivalent to the level of terpene product produced by a strain of the eukaryotic microbial host expressing the terpene synthase gene that requires a sterol in the medium for growth.

In the present invention, the step of isolating a wild-type ERG9 gene to produce an isolated wild-type ERG9 gene is typically performed by amplifying a wild-type ERG9 gene by using a nucleic acid amplification process to produce an amplified wild-type ERG9 gene; however, other isolation methods are known in the art and are contemplated by this invention, it is not necessary to use PCR or another nucleic acid amplification method. When a nucleic acid amplification process is used, the nucleic acid amplification method is typically PCR. However, other nucleic acid amplification processes can be used that are well known in the art. In this method, the ERG9 gene can be a fungal ERG9 gene, such as a *Saccharomyces cerevisiae* ERG9 gene or an ERG9 gene of another *Saccharomyces* species; alternatively, the ERG9 gene can be any homologous ERG9 gene as described above. In this method, the mutagenesis is typically performed using error-prone PCR, although other mutagenesis methods are well known in the art and can alternatively be used. Such mutagenesis methods include, for example, ultraviolet (UV) radiation, ethyl methanesulfonate (EMS), nitrosoguanidine, and other mutagens.

When error-prone PCR is used, the error-prone PCR is typically performed using one or more DNA polymerase enzymes that have higher misinsertion and misextension rates than wild-type polymerase enzymes.

In the present invention, the terpene synthase gene that produces a detectable and measurable terpene product can be, for example, the *Hyoscyamus muticus* premnaspirodiene synthase (HPS) gene. Preferably, the terpene synthase gene that produces a detectable and measurable terpene product is one that produces a product detectable and measurable by gas chromatography, although other detection methods can be used.

In the present invention, a suitable strain of *S. cerevisiae* that contains a plasmid expressing a terpene synthase gene that produces a detectable and measurable terpene product is ALX7-95 (his3, trp1, erg9::HIS3, HMGcat/TRP1::rDNA, dpp1), a leucine prototroph of strain CALI-5 (U.S. Pat. Nos. 6,531,303 and 6,689,593), containing a plasmid expressing the *Hyoscyamus muticus* premnaspirodiene synthase (HPS) gene. Transformants of this strain require histidine for growth; before transformation, this strain requires supplementation with a sterol.

Although the invention can be used with isolates of mutations in *S. cerevisiae*, analogous methods can be used with other organisms, as described above.

Another aspect of the present invention is a method of isolating a variant squalene synthase enzyme. The variant squalene synthase enzyme to be isolated by these methods is as described above.

In general, this method comprises the steps of:

(1) culturing a host cell that expresses a variant squalene synthase enzyme or that contains a variant squalene synthase enzyme; and (2) isolating the variant squalene synthase enzyme from the host cell.

Typically, this method further comprises the step of purifying the isolated variant squalene synthase enzyme. Variant squalene synthase enzymes according to the present invention can be purified by conventional protein purification techniques, including, for example, techniques such as precipitation with salts such as ammonium sulfate, ion exchange chromatography, gel filtration, affinity chromatography, electrophoresis, isoelectric focusing, isotachophoresis, chromatofocusing, and other techniques are well known in the art and are described in R. K. Scopes. "Protein Purification: Principles and Practice" (3$^{rd}$ ed., Springer-Verlag, New York (1994)).

Yet another aspect of the present invention is a method of producing an isoprenoid using a mutated ERG9 gene, in which the defective ERG9 gene encodes a variant squalene synthase enzyme.

In one aspect of the invention a host cell that includes a mutated ERG9 gene encoding a variant squalene synthase enzyme further includes at least one isoprenoid synthase gene, so that the farnesyl pyrophosphate produced in the host cell, which is available in greater concentrations for isoprenoid biosynthesis can be converted to an isoprenoid by the isoprenoid synthase encoded by the isoprenoid synthase gene. For example, and not by way of limitation, the isopsenoid synthase gene included in the host cell can be a chimeric isoprenoid synthase gene such as those described in U.S. Patent Application Publication No. 2008/0178354. These chimeric isoprenoid synthase genes include derivatives of the *Hyoscyamus muticus* vetispiradiene synthase gene and/or the *Nicotiana tabacum* 5-epi-aristolochene synthase gene. Alternatively, the isoprenoid synthase gene included in the host cell can be a citrus valencene synthase gene as described in U.S. Patent Application Publication No. 2006/0218661. As yet another alternative, the isoprenoid synthase gene included in the host cell can be a *H. muticus* premnaspirodiene synthase gene, such as those described in Back and Chappell, J. Biol. Chem. 270: 7375-7381 (1995); Back and Chappell, PNAS USA 93: 6841-6845 (1996); and Greenhagen et al., PNAS USA 103: 9826-9831 (2006). As another alternative, the isoprenoid synthase gene included in the host cell can be an isoprenoid synthase gene such as those described in U.S. Patent Application Publication No. 2005/0210549. These isoprenoid synthase genes include 5-epi-aristolochene synthase from *Capsicum annuum*, (E)-β-farnesene synthase from *Mentha piperita*, δ-selenene synthase and γ-humulene synthase from *Abies grandis,* 6-cadinene synthase from *Gossypium arboretum*, E-α-bisabolene synthase from *Abies grandis*, germacrene C synthase from *Lycopersicon esculentum*, epi-cedrol synthase and amorpha-4,11-diene synthase from *Artemisia annua*, and germacrene A synthases from *Lactuca sativa, Cichorium intybus* and *Solidago canadensis*. Other suitable isoprenoid synthase genes are known in the art. In addition, mutants and protein engineered variants of these enzymes can be used. Methods for engineering variants of terpene synthases are known in the art; such methods can, for example, involve recombining domains from two or more terpene synthases to generate a chimeric terpene synthase. Such methods are described, for example, in U.S. Patent Application Publication No. 2006/0218661 and in U.S. Patent Application Publication No. 2008/0178354.

Accordingly, this aspect of the invention comprises the steps of:

(1) providing a host cell including a mutated ERG9 gene according to the present invention and at least one isoprenoid synthase gene;

(2) allowing the host cell to produce farnesyl pyrophosphate and to synthesize the isoprenoid from the farnesyl pyrophosphate; and (3) isolating the isoprenoid synthesized by the host cell.

Methods for isolating the isoprenoid synthesized by the host cell are well known in the art. For example, when the isoprenoid is premnaspirodiene, the premnaspirodiene can be isolated by (i) sequestering the premnaspirodiene by binding it to a hydrophobic resin; (ii) and isolating the premnaspirodiene from the hydrophobic resin. Preferably, the hydrophobic resin is Amberlite® XAD-16 hydrophobic resin. Other hydrophobic resins within the scope of the present invention will be known to one of reasonable skill in the art. Typically, premnaspirodiene is isolated from the hydrophobic resin by methanol extraction. Other methods of isolating premnaspirodiene that are within the scope of the present invention will be known to one of reasonable skill in the art. Other isoprenoids can be isolated by similar methods well known in the art, making use of the fact that isoprenoids are hydrophobic and bind to hydrophobic resins.

In an alternative for isolation of premnaspirodiene, a two-phase system can be used with a non-polar solvent, substantially immiscible with an aqueous phase, added to the fermentation broth and the premnaspirodiene removed from the non-polar phase by distillation. A preferred non-polar solvent is an oil. A particularly preferred oil is a vegetable oil such as soybean oil. Alternative non-polar solvents include, but are not limited to, high molecular weight aliphatic hydrocarbons such as, but not limited to, dodecane, tridecane, tetradecane, pentadecane, and hexadecane; either straight-chain or branched-chain isomers can be used; these high-molecular weight aliphatic hydrocarbons are optionally substituted with one or more hydroxy or halogen substituents as long as the substituted hydrocarbon remains substantially immiscible with the aqueous phase.

In this method, where commercial production of the isoprenoid is desired, a variety of fermentation methodologies may be applied. For example, large scale production may be effected by either batch or continuous fermentation. A classical batch fermentation is a closed system where the composition of the medium is set at the beginning of the fermentation and not subject to artificial alterations during the fermentation. Thus, at the beginning of the fermentation the medium is inoculated with the desired microorganism or microorganisms and fermentation is permitted to occur without further addition of nutrients. Typically, the concentration of the carbon source in a batch fermentation is limited, and factors such as pH and oxygen concentration are controlled. In batch systems the metabolite and biomass compositions of the system change constantly up to the time the fermentation is stopped. Within batch cultures cells typically modulate through a static lag phase to a high growth log phase and finally to a stationary phase where growth rate is diminished or halted. If untreated, cells in the stationary phase will eventually die.

A variation on the standard batch system is the Fed-Batch system. Fed-Batch fermentation processes are also suitable for use in the present invention and comprise a typical batch system with the exception that nutrients are added as the fermentation progresses. Fed-Batch systems are useful when catabolite repression is apt to inhibit the metabolism of the cells and where it is desirable to have limited amounts of substrate in the medium. Also, the ability to feed nutrients will often result in higher cell densities in Fed-Batch fermentation processes compared to Batch fermentation processes. Factors such as pH, dissolved oxygen, nutrient concentrations, and the partial pressure of waste gases such as $CO_2$ are generally measured and controlled in Fed-Batch fermentations. Batch and Fed-Batch fermentations are common and well known in the art and examples may be found in Brock, Biotechnology: A Textbook of Industrial Microbiology, 2nd ed.; Sinauer Associates: Sunderland, Mass. (1989); or Deshpande, Appl. Biochem. Biotechnol. 36:227 (1992).

Commercial production of the isoprenoid may also be accomplished with continuous fermentation. Continuous fermentation is an open system where a defined fermentation medium is added continuously to a bioreactor and an equal amount of conditioned medium is removed simultaneously for processing. This system generally maintains the cultures at a constant high density where cells are primarily in their log phase of growth. Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems strive to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

Microorganism host cells useful in the present invention for the production of the isoprenoid may include, but are not limited to, bacteria, such as the enteric bacteria (*Escherichia* and *Salmonella* for example) as well as *Bacillus, Acinetobacter, Streptomyces, Methylobacter, Rhodococcus* and *Pseudomonas*; Cyanobacteria, such as *Rhodobacter* and *Synechocystis*; yeasts, such as *Saccharomyces, Zygosaccharomyces, Kluyveromyces, Candida, Hansenula, Debaryomyces, Mucor, Pichia, Yarrowia*, and *Torulopsis*; and filamentous fungi such as *Aspergillus* and *Arthrobotrys*, and algae for example. Preferably, the host cell is a eukaryotic cell. More preferably, the host cell is a yeast cell, which is a eukaryotic microorganism host cell. Most preferably, the host cell is a *Saccharomyces cerevisiae* cell.

Microbial expression systems and expression vectors containing regulatory sequences that direct high level expression of foreign proteins are well known to those skilled in the art. These expression systems and expression vectors are known both for prokaryotic organisms such as bacteria and for eukaryotic organisms such as yeast. Similarly, vectors or cassettes useful for the transformation of suitable microbial host cells are well known in the art. These vectors and cassettes are known both for prokaryotic organisms such as bacteria and for eukaryotic organisms such as yeast. Typically, the vector or cassette contains sequences directing expression of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination.

Initiation control regions or promoters, which are useful to drive expression of the relevant genes in the desired host cell are numerous and familiar to those skilled in the art. Termination control regions may also be derived from various genes native to the preferred hosts.

Expression of cloned heterologous genes in yeast cells, particularly cells of *S. cerevisiae*, is described in the following references: Emr, Meth. Enzymol. 185: 231-233 (1991), is a general overview of expression in yeast, including the possibility of exploiting protein secretion and modification in yeast and achieving stability of expressed proteins. Rose and Broach, Meth. Enzymol. 185: 234-279 (1991), describes the use of 2-μm circle-based vectors for transfection of genes into yeast and for expression of heterologous genes in yeast, including standard 2-μm circle-based vectors, vectors for high copy propagation, vectors for expression of cloned genes in yeast, and vectors for specialized applications. Stearns et al., Meth. Enzymol. 185: 280-297 (1991), describes the use of yeast vector systems and components, the use of homologous recombination to integrate plasmids into the yeast host genome, and the use of centromere plasmids. Mylin et al., Meth. Enzymol. 185: 297-308 (1991), describes the use of galactose-inducible promoters to provide high levels of production of cloned proteins in yeast. Price et al., Meth. Enzymol. 185: 308-318 (1991), describes the use of the glucose-repressible ADH2 promoter to provide controllable, high level expression of cloned proteins in yeast. Etcheverry, Meth. Enzymol. 185: 319-329 (1991), describes the use of the yeast CUP1 promoter to drive controllable expression of cloned genes in yeast. Kingsman et al., Meth. Enzymol. 185: 329-341 (1991), describes the use of the yeast PGK promoter to drive controllable expression of cloned genes in yeast. Rosenberg et al., Meth. Enzymol. 185: 341-350 (1991), describes the use of expression cassette plasmids utilizing the strong GAPDH-491 promoter for high levels of heterologous protein production in yeast. Sledziewski et al., Meth. Enzymol. 185: 351-366 (1991), describes the construction of temperature-regulated variants of two strong yeast promoters, TPI1 and ADH2, and the use of these promoters for regulation of expression and thus regulation of the extent of glycosylation of proteins secreted by yeast. Donahue and Cigan, Meth. Enzymol. 185: 366-372 (1991), describes the significance of codon usage variations between yeast and higher eukaryotes and the selection of efficient leader sequences. Jones, Meth. Enzymol. 185: 372-386 (1991), describes the elimination of vacuolar protease activity in yeast to maximize the yield of protein production from cloned genes. Wilkinson, Meth. Enzymol. 185: 387-397 (1991), describes methods for preventing ubiquitin-dependent protein degradation in yeast, again to maximize the yield of protein production from cloned genes. Kendall et al., Meth. Enzymol. 185: 398-407 (1991), describes the cotranslational processing events that occur in yeast at the amino-termini of nascent polypeptide genes and their effects on heterologous gene expression and protein stability. Brake, Meth. Enzymol. 185: 408-421 (1991), describes expression systems based on the yeast α-factor leader. Hitzeman et al., Meth. Enzymol. 185: 421-440 (1991), describes the use of both heterologous and homologous signal sequences for the production and secretion of heterologous gene products in yeast. Chisholm et al., "Meth. Enzymol. 185: 471-482 (1991), describes the use of an enhanced secretion phenotype occurring among drug-resistant yeast mutants to maximize secretion of cloned proteins in yeast.

General molecular biological techniques of gene cloning, site-directed mutagenesis and fusion protein construction can be used to provide nucleic acid segments that include therein the isoprenoid synthase gene. Typically, the nucleic acid segments are DNA nucleic acid segments. Typically, as described above, the isoprenoid synthase gene is operatively linked to at least one nucleic acid expression control element, such as, but not limited to, a promoter, an enhancer, or a site capable of binding a repressor or activator. Such nucleic acid expression control elements are well known in the art. Typically, as described above, the isoprenoid synthase gene is included in a vector and, as such, is again operatively linked to at least one nucleic acid expression control element. Site-directed mutagenesis can be used, for example, to provide optimum codon selection for expression in *S. cerevisiae*, as described above. The isoprenoid synthase gene can, in one alternative, be expressed in the form of a nucleic acid segment encoding a fusion protein, such as a purification tag or other detectable protein domain.

In another alternative method for producing an isoprenoid, the method, in general, comprises the steps of:

(1) providing a host cell including a mutated ERG9 gene according to the present invention;
(2) allowing the host cell to produce farnesyl pyrophosphate
(3) isolating farnesyl pyrophosphate from the host cell;
(4) reacting the farnesyl pyrophosphate in vitro with one or more isoprenoid synthases to synthesize the isoprenoid; and
(5) isolating the isoprenoid.

As described above, a number of isoprenoid synthases are available for in vitro use. These isoprenoid synthases have been either cloned or isolated from plants. The step of isolating the isoprenoid is performed as described above.

In both of these synthesis methods, additional reactions can be performed on the isolated isoprenoid to transform the isolated isoprenoid into another isoprenoid or related compound. These additional reactions can be reactions such as oxidation, hydroxylation, alkylation, halogenation, or other reactions well known in the art. In particular, reactions such as hydroxylation or oxidation can be carried out by cytochrome P450 enzymes. These reactions, and methods of carrying them out by chemical or enzymatic means, are well known in the art and need not be described further here.

The present invention describes improved strains of *Saccharomyces cerevisiae* that have a defective squalene synthase enzyme. These strains have the ability to produce enough squalene so that they do not need to be supplemented with sterols such as ergosterol for growth. However, because these strains produce less squalene than do wild-type strains, they have more farnesyl pyrophosphate available for eventual isoprenoid synthesis, because farnesyl pyrophosphate is a branch point for the steroid synthesis and isoprenoid synthesis pathways. Therefore, these strains, as well as the nucleic acid segments encoding the defective squalene synthase enzyme and the defective squalene synthase enzymes themselves, are useful for the improved production of isoprenoid products because the strains of *S. cerevisiae* do not need to be supplemented with sterols for growth and can produce high levels of farnesyl pyrophosphate without such supplementation.

Because the eventual isoprenoid products have commercial value as antibiotics, pest control agents, fragrances, flavors, and anti-cancer agents, the nucleic acid segments, eukaryotic microbial host cell strains, including *S. cerevisiae* strains, vectors and host cells incorporating the nucleic acid segments, and the variant squalene synthase enzymes have industrial utility.

The invention is illustrated by the following examples. These examples are for illustrative purposes only, and are not intended to limit the invention.

EXAMPLES

Example 1

Generation of Mutant ERG9 Genes

Chromosomal DNA isolated from *Saccharomyces cerevisiae* strain ATCC28383 was used as the DNA template for PCR amplification of the wild type ERG9 gene. The primers used for the amplification were the upstream primer 7-162.1 5'-CCATCTTCAACAACAATACCG-3' (SEQ ID NO: 1) (underlined nucleotides at the 5' end of the ERG9 sequence in FIGS. 2A-2D) and the downstream primer 7-162.2 5'-GTACTTAGTTATTGTTCGG-3' (SEQ ID NO: 2) (underlined nucleotides at the 3' end of ERG9). Using Taq polymerase (New England Biolabs), amplification conditions were 94° C. for 30 seconds, 45° C. for 30 seconds, 72° C. for 2 minutes for a total of 30 cycles. The resulting ERG9 PCR product was sequenced and verified to be identical to the published sequence for ERG9. This DNA was used as the template for performing error prone PCR using the GeneMorph kit from Stratagene and the same primers described above. The error-prone PCR reaction was run using two different DNA concentrations (~500 ng and ~50 ng) to generate a range of mutations per gene. This generated a pool of ERG9 mutant genes.

Example 2

Isolation of erg9$^{def}$ Mutants

To isolate ERG9 mutants that make sufficient ergosterol to restore growth, the PCR product from the mutagenic PCR reaction was transformed into ALX7-95 (his3, trp1, erg9::HIS3, HMGcat/TRP1:rDNA, dpp1), a leucine prototroph of strain CALI-5 (U.S. Pat. Nos. 6,531,303 and 6,689,593), containing a plasmid expressing the *Hyoscyamus muticus* premnaspirodiene synthase (HPS) gene. The HPS gene was cloned into the yeast shuttle expression vector YEp-GW-URA-NheI/BamHI to give YEp-HPS-ura. This vector contained the ADH1 promoter for initiating transcription of the HPS gene. In addition, it contained the ADH1 terminator downstream of the HPS gene. This vector was maintained in *S. cerevisiae* by selecting media lacking uracil and it was maintained in *E. coli* by selecting for resistance to ampicillin.

Transformation procedure of this strain with the ERG9 mutant pool used the lithium acetate transformation kit from Sigma. Transformants were selected for growth on YPD medium (10 g/L yeast extract, 20 g/L peptone, 20 g/L glucose) without ergosterol. Since the parent strain requires ergosterol for growth, transformants that grew on YPD replaced the erg9::HIS3 replacement mutation with a copy of ERG9 that made sufficient amount of ergosterol for growth. This was verified by the fact that transformants had obtained a requirement for histidine for growth.

To screen for premnaspirodiene production in strains transformed with ERG9 mutant genes, a high-throughput screening procedure using microvial cultures was employed. Transformant yeast colonies were inoculated into individual wells of 96-well microtiter plates filled with 200 μL of SD (0.67 Bacto yeast nitrogen base without amino acids, 2% glucose, 0.14% yeast synthetic drop-out medium without uracil). The plate was grown for two days at 28° C. After growth to saturation, ten μL from each well was used to inoculate in duplicate two ml glass vials containing 250 μL of medium suitable for growth and premnaspirodiene production. The vials were sealed with serum-stoppered caps and then incubated with shaking for 3 days. The products were extracted first by introducing 250 μL of acetone through the serum stopper and vortexing, followed by addition of 500 μl of n-hexane and vortexing. After phase separation, the vials were placed on the sample tray of a gas chromatography autosampler, which removed one microliter of the organic phase for analysis of premnaspirodiene. The acetone and hexane used for extraction were each spiked with internal standards to aid in quantitation of the samples. The extracted samples were analyzed by GC and the amount of premnaspirodiene was calculated from the peak area.

Several mutant strains were identified that produced more or similar amounts of premnaspirodiene as the control strain ALX7-95 containing expressed HPS. They were given the designations ALX7-168.4, ALX7-168.10, ALX7-168.14, ALX7-168.19, ALX7-168.22, ALX7-168.23, ALX7-168.24, ALX7-168.25, and ALX7-183.69. The ERG9 gene from these mutant strains was PCR amplified and the PCR product was sequenced to determine the mutations within each strain. A HIS3+ strain of ALX7-168.25 was constructed and is designated ALX7-175.1.

Example 3

Production of Premnaspirodiene in Fermentors

As described in Example 2, strain ALX7-175.1 was constructed for the production of premnaspirodiene. Production of premnaspirodiene in this strain was compared to that of strain ALX7-95 HPS, which is completely lacking in squalene synthase activity.

Production of premnaspirodiene was carried out in a 3-L fermentation tank (New Brunswick Bioflow 110). One liter of fermentation medium was prepared and autoclaved in the fermentation tank (20 g $(NH_4)_2SO_4$, 20 g $KH_2PO_4$, 1 g NaCl, $MgSO_4.7H_2O$, 4 g yeast extract (Difco). Afterward the following components were added: 20 ml mineral solution (0.028% $FeSO_4.7H_2O$, 0.029% $ZnSO_4.7H_2O$, 0.008% $CuSO_4.5H_2O$, 0.024% $Na_2MoO_4.2H_2O$, 0.024% $CoCl_2.6H_2O$, 0.017% $MnSO_4.H_2O$, 1 mL HCl); 10 mL 50% glucose; 30 mL vitamin solution (0.001% biotin; 0.012% calcium pantothenate, 0.06% inositol, 0.012% pyridoxine-HCl, 0.012% thiamine-HCl); 10 mL 10% $CaCl_2$, and 20 mL autoclaved soybean oil (purchased from local groceries). For ALX7-95 HPS, 1 mL of 50 mg/mL cholesterol in 100% ethanol was added.

The seed culture for inoculating the fermentation medium was prepared by inoculating 50 mL of SD medium for ERG9 transformant strains. Non-transformant control cultures were grown in SDE medium (SD medium supplemented with 40 mg/L ergosterol). This culture was grown until early stationary phase (24-48 hr). One mL of this culture was inoculated into 500 mL of SD or SDE medium, as appropriate, and grown for 24 hr. A 50-mL aliquot (5% inoculum) was used to inoculate the one liter of medium.

The fermentor was maintained at 26° C. The air flow was 4.5 L/min and the $dO_2$ was maintained above 30% by adjusting the rpm. Furthermore, the pH was maintained at 4.5 using acetic acid and NaOH.

Once the glucose concentration was below 1 g/L, a feeding regimen was initiated such that the glucose in the fermentor was kept between 0 and 1 g/L. The glucose feed was made by mixing 1400 mL of 60% glucose and 328 mL of 12.5% yeast extract.

After 5 days, the air and agitation were turned off, and the oil was allowed to rise to the top of the tank and decanted.

Example 4

Comparison of Premnaspirodiene Production in erg9 Mutants and erg9::HIS3 Strains in Microvial Cultures As described in Example 2, initial screening of mutants was conducted using microvial cultures. Mutants were further screened in microvial cultures by growing in media with or without 40 mg/L ergosterol supplementation and compared to ALX7-95 HPS grown with ergosterol (ALX7-95 HPS will not grow without ergosterol). Twenty-five isolates are compared in FIG. 1. In FIG. 1, the concentration of premnaspirodiene in mg/L is shown for each of the 25 isolates with and without ergosterol supplementation. Several of these isolates produced more or comparable amounts of premnaspirodiene as the control culture ALX7-95 HPS. In general, these strains produced more premnaspirodiene in the absence of ergosterol than in its presence. Isolates 4, 10, 14, 19, 22, 23, 24, 25, and 69 were given strain designations ALX7-168.4, ALX7-168.10, ALX7-168.14, ALX7-168.19, ALX7-168.22, ALX7-168.23, ALX7-168.24, ALX7-168.25, and ALX7-83.169 respectively.

Example 5

Comparison of Premnaspirodiene Production in erg9 Mutants and erg9::HIS3 Strains in Fermentation Cultures In this example, strains ALX7-95 HPS (erg9::HIS3) and ALX7-175.1, a histidine prototroph of ALX7-168.25 ($erg9^{def}$) were grown in fermentors using the same protocol except for the presence or absence of cholesterol in the medium. At the end of the fermentation, premnaspirodiene was assayed by gas chromatography. As indicated in Table 1, the yields of premnaspirodiene in the fermentors was similar. However, because of faster growth and growth to higher density of the $erg9^{def}$ strain, more glucose was fed and consumed during the course of the fermentation. Because of the resultant higher volume, more total premnaspirodiene was produced by the $erg9^{def}$ culture grown under the same starting conditions.

TABLE 1

| Strain | ERG9 Allele | Cell Density, $OD_{600}$ | Premnaspirodiene Titer, g/L | Final Volume, Liters | Total Yield, grams |
|---|---|---|---|---|---|
| ALX7-95 HPS | erg9::HIS3 | 48 | 3.9 | 1.1 | 4.3 |
| ALX7-175.1 | $erg9^{def}$25 | 193 | 3.7 | 1.7 | 6.2 |

Example 6

Sequences of $erg9^{def}$ Mutants

The sequence of the wild type ERG9 gene and sequences 245 base pairs upstream are shown in FIGS. 2A-2D. The ERG9 alleles from strains described in Examples 2 and 4 were obtained by PCR amplification of genomic DNA from strains designations ALX7-168.4, ALX7-168.10, ALX7-168.14, ALX7-168.19, ALX7-168.22, ALX7-168.23, ALX7-168.24, ALX7-168.25, and ALX7-183.69. The resulting DNA was sequenced, and the sequences corresponding to those mutants are shown in Table 2. All mutant genes contain mutations in the ERG9 coding region. Alleles 10, 23, 24, and 25 contain, in addition, mutations in the 245 base pair non-coding region of upstream of the gene.

TABLE 2

| Mutant | Nucleotide position and change | Amino Acid position and change | Affect of change on amino acid |
|---|---|---|---|
| 4 | 691 A→G | 149 E→G | |
| | 748 G→T | 168 G→V | |
| | 786 T→A | 181 Y→N | |
| | 1114 A→T | 290 Q→L | |
| | 1213 T→C | 323 I→T | |
| | 1290 T→C | 349 L→L | silent |

TABLE 2-continued

| Mutant | Nucleotide position and change | Amino Acid position and change | Affect of change on amino acid |
|---|---|---|---|
| 10 | 72 C→A | | non-coding |
| | 110 Δ A | | non-coding |
| | 801 G→A | 186 V→I | |
| 14 | 989 T→A | 248 P→P | silent |
| | 1112 G→A | 289 E→E | silent |
| | 1220 G→A | 325 K→K | silent |
| | 1233 T→C | 330 Y→H | |
| 19 | 786 T→A | 181 Y→N | |
| | 1025 A→G | 260 Q→Q | silent |
| | 1056 T→A | 271 L→I | |
| | 1068 A→G | 275 S→G | |
| | 1203 A→G | 320 N→D | |
| 22 | 886 T→C | 214 M→T | |
| | 969 A→G | 242 I→V | |
| | 1075 T→C | 277 V→A | |
| | 1114 A→T | 290 Q→L | |
| 23 | 84 T→A | | non-coding |
| | 283 A→T | 13 E→V | |
| | 424 T→C | 60 L→P | |
| | 440 A→G | 65 R→R | silent |
| | 1076 T→C | 277 V→V | silent |
| 24 | 619 A→T | 125 D→V | |
| | 634 T→C | 130 L→P | |
| | 962 C→T | 239 P→P | silent |
| 25 | 150 A→T | | non-coding |
| | 410 T→G | 55 A→A | silent |
| | 411 G→T | 56 V→L | |
| | 1248 T→C | 335 S→P | |
| 69 | 510 C→T | 89 H→Y | |
| | 573 T→C | 110 F→L | |
| | 918 A→G | 224 R→G | |
| | 997 A→G | 251 K→G | |

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

We claim:

1. A method of isolating a defective ERG9 gene that permits growth of a host in sterol-free medium and production of terpenes in sterol-free medium, comprising:
   (a) isolating a wild-type ERG9 gene to produce an isolated wild-type ERG9 gene;
   (b) subjecting the isolated wild-type ERG9 gene to mutagenesis to generate a pool of ERG9 mutants, wherein the pool comprises ERG9 mutants that encode variant squalene synthase enzymes that comprise one or more amino acid substitution(s) compared to the wild-type squalene synthase enzyme;
   (c) transforming mutants from the pool of erg9 mutants generated in step (b) into a strain of a eukaryotic microbial host that contains an expressed terpene synthase gene that produces a detectable and measurable terpene product, the strain of the eukaryotic microbial host being transformed in such a manner that replacement of the preexisting ERG9 allele with an erg9 mutation allows the strain to grow in a sterol-free medium;
   (d) growing the transformants in sterol-free medium; and
   (e) selecting a transformant from step (d) that grows in sterol-free medium and produces a terpene product in the sterol-free medium and isolating the defective ERG9 gene from the transformant.

2. The method of claim 1, wherein the step of isolating the wild-type ERG9 gene is performed by a nucleic amplification method.

3. The method of claim 1, wherein the ERG9 gene is a fungal ERG9 gene.

4. The method of claim 3, wherein the fungal ERG9 gene is a *Saccharomyces* ERG9 gene.

5. The method of claim 4, wherein the *Saccharomyces* ERG9 gene is a *Saccharomyces cerevisiae* ERG9 gene.

6. The method of claim 1, wherein the mutagenesis is carried out by performing error-prone PCR.

7. The method of claim 6, wherein the error-prone PCR is performed using one or more DNA polymerase enzymes that have higher misinsertion and misextension rates than wild-type polymerase enzymes.

8. The method of claim 1, wherein the eukaryotic microbial host is a fungal microbial host.

9. The method of claim 8, wherein the fungal microbial host is a yeast microbial host.

10. The method of claim 9, wherein the yeast microbial host is a yeast of the genus *Saccharomyces*.

11. The method of claim 10, wherein the yeast of the genus *Saccharomyces* is *Saccharomyces cerevisiae*.

12. The method of claim 1, wherein the terpene synthase gene that produces a detectable and measurable terpene product is a *Hyoscyamus muticus* premnaspirodiene synthase (HPS) gene.

13. The method of claim 1, wherein the terpene synthase gene that produces a detectable and measurable terpene product is one that produces a product detectable and measurable by gas chromatography.

14. The method of claim 11, wherein the strain of *S. cerevisiae* that contains an expressed terpene synthase gene that produces a detectable and measurable terpene product is ALX7-95 (his3, trp1, erg9::HIS3, HMGcat/TRP1::rDNA, dpp1), a leucine prototroph of strain CALI-5, that contains a plasmid expressing the *Hyoscyamus muticus* premnaspirodiene synthase (HPS) gene.

15. A method of isolating a variant squalene synthase enzyme, comprising:
(a) culturing host cells that express the variant squalene synthase enzyme that, when present and expressed in vivo in a eukaryotic microbial host as the only squalene synthase species, catalyzes the synthesis of squalene at a sufficiently high rate that supplementation of the host cell with a sterol is not required for growth, wherein the host cell is cultured in medium lacking a sterol;
(b) selecting a host cell that grows in medium lacking a sterol, and also produces a terpene product; and
(c) isolating the variant squalene synthase enzyme from the host cell, wherein:
the isolated variant squalene synthase enzyme comprises one or more amino acid substitution(s) compared to a wild-type squalene synthase enzyme, and exhibits reduced cellular squalene synthase activity compared to the wild-type enzyme that does not comprise the one or more amino acid substitution(s); and
a host cell expressing such enzyme produces a terpene product in the absence of sterol supplementation.

16. The method of claim 15, wherein the method further comprises the step of purifying the isolated variant squalene synthase enzyme.

17. The method of claim 15 wherein the variant squalene synthase enzyme is a variant *Saccharomyces cerevisiae* squalene synthase enzyme.

18. A method of producing an isoprenoid using a eukaryotic microbial host comprising a mutated ERG9 gene, wherein:
the mutated ERG9 gene encodes a variant squalene synthase enzyme that comprises one or more amino acid substitutions compared to a wild-type squalene synthase enzyme;
the variant squalene synthase enzyme exhibits reduced cellular squalene synthase activity compared to the enzyme that does not comprise the one or more amino acid substitution(s), whereby:
the variant squalene synthase enzyme, when present and expressed in vivo in the eukaryotic microbial host as the only squalene synthase species, catalyzes the synthesis of squalene at a sufficiently high rate that supplementation of the eukaryotic microbial host with a sterol is not required for growth; and the method comprises the steps of:
(a) providing a host cell that includes a mutated ERG9 gene that encodes the variant squalene synthase enzyme and at least one isoprenoid synthase gene;
(b) allowing the host cell to produce farnesyl pyrophosphate in medium lacking a sterol and to synthesize the isoprenoid from the farnesyl pyrophosphate in the medium lacking a sterol; and
(c) isolating the isoprenoid synthesized by the host cell.

19. The method of claim 18, wherein the host cell is a *Saccharomyces cerevisiae* cell.

20. The method of claim 18, wherein the variant squalene synthase enzyme is a variant *Saccharomyces cerevisiae* squalene synthase enzyme.

21. The method of claim 18, wherein the isoprenoid synthase gene is selected from the group consisting of the *Hyoscyamus muticus* vetispiradiene synthase gene, the *H. muticus* premnaspirodiene synthase gene, the *Nicotiana tabacum* 5-epi-aristolochene synthase gene, a citrus valencene synthase gene, the *Capsicum annuum* 5-epi-aristolochene synthase gene, the *Mentha piperita* E-β-farnesene synthase gene, the *Abies grandis* δ-selenene synthase gene, the *Abies grandis* γ-humulene synthase gene, the *Abies grandis*-α-bisabolene synthase gene, the *Gossypium arboretum* δ-cadinene synthase gene, the *Lycopersicon esculentum* germacrene C synthase gene, the *Artemisia annua* epi-cedrol synthase gene, the *Artemisia annua* amorpha-4,11-diene synthase gene, the *Lactuca sativa* germacrene A synthase gene, the *Cichorium intybus* germacrene A synthase gene, and the *Solidago canadensis* germacrene A synthase gene, and mutants and protein engineered variants thereof.

22. The method of claim 21, wherein the isoprenoid synthase gene is the *H. muticus* premnaspirodiene synthase gene and the isoprenoid produced is premnaspirodiene.

23. The method of claim 22, wherein the premnaspirodiene is isolated by (i) sequestering the premnaspirodiene by binding it to a hydrophobic resin; and (ii) isolating the premnaspirodiene from the hydrophobic resin.

24. The method of claim 22, wherein the premnaspirodiene is isolated by using a two-phase system in which a non-polar solvent, substantially immiscible with an aqueous phase, is added to the fermentation broth, the nonpolar solvent is separated from the aqueous phase of the fermentation broth, and the premnaspirodiene is removed from the non-polar phase by distillation.

25. The method of claim 24, wherein the non-polar solvent is an oil.

26. The method of claim 18 further comprising the step of performing at least one additional reaction on the isolated isoprenoid in order to transform the isolated isoprenoid into another isoprenoid or related compound.

27. The method of claim 26, wherein the at least one additional reaction is selected from the group consisting of oxidation, hydroxylation, alkylation, and halogenation.

28. The method of claim 27, wherein the at least one additional reaction is an oxidation or hydroxylation and is carried out by use of a cytochrome P450 enzyme.

29. A method of producing an isoprenoid comprising the use of a mutated ERG9 gene, wherein:
the mutated ERG9 gene encodes a variant squalene synthase enzyme that comprises one or more amino acid substitutions compared to a wild-type squalene synthase enzyme;

the variant enzyme exhibits reduced cellular squalene synthase activity compared to the enzyme that does not comprise the one or more amino acid substitution(s), whereby:

the variant squalene synthase enzyme, when present and expressed in vivo in a eukaryotic microbial host as the only squalene synthase species, catalyzes the synthesis of squalene at a sufficiently high rate that supplementation of the eukaryotic microbial host with a sterol is not required for growth; and the method comprises the steps of:
(a) providing a host cell that includes a mutated ERG9 gene that encodes the variant squalene synthase enzyme;
(b) allowing the host cell to produce farnesyl pyrophosphate in medium lacking a sterol;
(c) isolating farnesyl pyrophosphate from the host cell;
(d) reacting the farnesyl pyrophosphate in vitro with one or more isoprenoid synthases to synthesize the isoprenoid; and
(e) isolating the isoprenoid.

30. The method of claim 29, wherein the host cell is a *Saccharomyces cerevisiae* cell.

31. The method of claim 30, wherein the variant squalene synthase enzyme is a variant *Saccharomyces cerevisiae* squalene synthase enzyme.

32. The method of claim 30 wherein the isoprenoid synthase is selected from the group consisting of the *Hyoscyamus muticus* vetispiradiene synthase, the *H. muticus* premnaspirodiene synthase, the *Nicotiana tabacum* 5-epi-aristolochene synthase, a citrus valencene gene, the *Capsicum annuum* 5-epi-aristolochene synthase, the *Mentha piperita* E-β-farnesene synthase, the *Abies grandis* δ-selenene synthase, the *Abies grandis* γ-humulene synthase, the *Abies grandis*-α-bisabolene synthase, the *Gossypium arboretum* 6-cadinene synthase, the *Lycopersicon esculentum* germacrene C synthase, the *Artemisia annua* epi-cedrol synthase, the *Artemisia annua* amorpha-4,11-diene synthase, the *Lactuca sativa* germacrene A synthase, the *Cichorium intybus* germacrene A synthase, and the *Solidago canadensis* germacrene A synthase, and mutants and protein engineered variants thereof.

33. The method of claim 32, wherein the isoprenoid synthase is the *H. muticus* premnaspirodiene synthase and the isoprenoid produced is premnaspirodiene.

34. A method of producing an isoprenoid using a eukaryotic microbial host comprising a mutated ERG9 gene, wherein:

the mutated ERG9 gene encodes a variant squalene synthase enzyme that comprises one or more amino acid substitutions compared to a wild-type squalene synthase enzyme;

the variant squalene synthase enzyme, when present and expressed in vivo in the eukaryotic microbial host as the only squalene synthase species, catalyzes the synthesis of squalene at a sufficiently high rate that supplementation of the eukaryotic microbial host with a sterol is not required for growth and results in reduced cellular squalene synthase activity compared to wild-type enzyme;

the method comprises the steps of:
(a) providing a *Saccharomyces cerevisiae* host cell that includes a mutated ERG9 gene that encodes the variant squalene synthase enzyme;
(b) allowing the host cell to produce farnesyl pyrophosphate;
(c) isolating farnesyl pyrophosphate from the host cell;
(d) reacting the farnesyl pyrophosphate in vitro with one or more isoprenoid synthases to synthesize the isoprenoid, wherein an isoprenoid synthase is the *H. muticus* premnaspirodiene synthase, and the isoprenoid produced is premnaspirodiene; and
(e) isolating the premnaspirodiene, by:
(i) sequestering the premnaspirodiene by binding it to a hydrophobic resin; and
(ii) isolating the premnaspirodiene from the hydrophobic resin.

35. A method of producing an isoprenoid using a host cell comprising a mutated ERG9 gene, wherein:

the mutated ERG9 gene encodes a variant squalene synthase enzyme that comprises one or more amino acid substitutions compared to a wild-type squalene synthase enzyme;

the variant squalene synthase enzyme, when present and expressed in vivo in the eukaryotic microbial host as the only squalene synthase species, catalyzes the synthesis of squalene at a sufficiently high rate that supplementation of the eukaryotic microbial host with a sterol is not required for growth and results in reduced cellular squalene synthase activity compared to wild-type enzyme;

the method comprises the steps of:
(a) providing a *Saccharomyces cerevisiae* host cell that includes a mutated ERG9 gene that encodes the variant squalene synthase enzyme;
(b) allowing the host cell to produce farnesyl pyrophosphate;
(c) isolating farnesyl pyrophosphate from the host cell;
(d) reacting the farnesyl pyrophosphate in vitro with one or more isoprenoid synthases to synthesize the isoprenoid, wherein an isoprenoid synthase is the *H. muticus* premnaspirodiene synthase, and the isoprenoid produced is premnaspirodiene; and
(e) isolating the premnaspirodiene, by: adding a nonpolar solvent, substantially immiscible with an aqueous phase, to the reaction of (d);

separating the nonpolar solvent from the aqueous phase of the reaction of (d); and removing the premnaspirodiene from the non-polar phase by distillation.

36. The method of claim 35, wherein the non-polar solvent is an oil.

37. The method of claim 31, further comprising the step of performing at least one additional reaction on the isolated isoprenoid in order to transform the isolated isoprenoid into another isoprenoid or related compound.

38. The method of claim 37, wherein the at least one additional reaction is selected from the group consisting of oxidation, hydroxylation, alkylation, and halogenation.

39. The method of claim 38, wherein the at least one additional reaction is an oxidation or hydroxylation and is carried out by use of a cytochrome P450 enzyme.

40. The method of claim 1, wherein the eukaryotic microbial host produces a terpene product in medium lacking a sterol such that the level of the terpene product is at least equivalent to the level of terpene product produced by the strain of the eukaryotic microbial host that requires a sterol.

41. The method of claim 15, wherein the host cell produces a terpene product in medium lacking a sterol such that the level of the terpene product is at least equivalent to the level of terpene product produced by the strain of the host cell that requires a sterol.

42. The method of claim 18, wherein the eukaryotic microbial host produces the isoprenoid in medium lacking a sterol such that the level of the isoprenoid product is at least equivalent to the level of isoprenoid product produced by the strain of the eukaryotic microbial host that requires a sterol.

43. The method of claim 29, wherein the host cell produces the farnesyl pyrophosphate in medium lacking a sterol such that the level of the farnesyl pyrophosphate is at least equivalent to the level of farnesyl pyrophosphate produced by the strain of the host cell that requires a sterol.

44. The method of claim 1, wherein the terpene product is farnesyl pyrophosphate or premnaspirodiene.

45. The method of claim 15, wherein the terpene product is farnesyl pyrophosphate.

46. The method of claim 18, wherein the isoprenoid is premnaspirodiene.

47. The method of claim 29, wherein the isoprenoid is premnaspirodiene.

48. The method of claim 1, further comprising, isolating the defective ERG9 gene.

49. The method of claim 1, wherein the eukaryotic microbial host grows in sterol-free medium and produces a terpene product in medium that is not supplemented with a sterol.

\* \* \* \* \*

UNITED STATES PATENT AND TRADEMARK OFFICE
CERTIFICATE OF CORRECTION

| | | |
|---|---|---|
| PATENT NO. | : 8,481,286 B2 | Page 1 of 1 |
| APPLICATION NO. | : 12/540094 | |
| DATED | : July 9, 2013 | |
| INVENTOR(S) | : Julien et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 556 days.

Signed and Sealed this
Eighth Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,481,286 B2
APPLICATION NO. : 12/540094
DATED : July 9, 2013
INVENTOR(S) : Julien et al.

It is certified that error appears in the above-identified patent and that said Letters Patent is hereby corrected as shown below:

IN THE TITLE PAGES:

In Item (56) References Cited, please add to the list of OTHER PUBLICATIONS --International Search Report and Written Opinion, issued March 8, 2010, in connection with International Patent Application No. PCT/US09/53589. 18 pages.--.

IN THE SPECIFICATION:

At column 6, lines 61-62, please replace "8-hydroxy-N6-methyladenosine" with --8-hydroxy-$N^6$-methyladenosine--;

at column 10, line 38, please replace "genes, Which when" with --genes, which when--;

at column 18, line 60, please replace "Ch. 7-9 (1988)" with --Ch. 7-9 (1988))--;

at column 21, line 56, please replace "pool of ERG9 erg9 mutants" with --pool of erg9 mutants--;

at column 23, line 13, please replace "biosynthesis can be converted" with --biosynthesis, can be converted--;

at column 23, line 37, please replace "6-cadinene synthase" with --δ-cadinene synthase--;

at column 26, line 43, please replace ""Meth. Enzymol." with --Meth. Enzymol.--;

at column 27, lines 3-4, please replace "farnesyl pyrophosphate" with --farnesyl pyrophosphate;--;

at column 29, line 19, please replace "yeast extract (Difco)" with --yeast extract (Difco))--.

Signed and Sealed this
Twenty-seventh Day of May, 2014

Michelle K. Lee
*Deputy Director of the United States Patent and Trademark Office*

CERTIFICATE OF CORRECTION (continued)
U.S. Pat. No. 8,481,286 B2

IN THE CLAIMS:

Column 41, line 28 to line 42 should read

32. The method of claim 30, wherein the isoprenoid synthase is selected from the group consisting of the *Hyoscyamus muticus* vetispiradiene synthase, the *H. muticus* premnaspirodiene synthase, the *Nicotiana tabacum* 5-epi-aristolochene synthase, a citrus valencene gene, the *Capsicum annuum* 5-epi-aristolochene synthase, the *Mentha piperita* E-β-farnesene synthase, the *Abies grandis* δ-selenene synthase, the *Abies grandis* γ-humulene synthase, the *Abies grandis*-α-bisabolene synthase, the *Gossypium arboretum* δ-cadinene synthase, the *Lycopersicon esculentum* germacrene C synthase, the *Artemisia annua* epi-cedrol synthase, the *Artemisia annua* amorpha-4,11-diene synthase, the *Lactuca sativa* germacrene A synthase, the *Cichorium intybus* germacrene A synthase, and the *Solidago canadensis* germacrene A synthase, and mutants and protein engineered variants thereof.

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
ccatcttcaa caacaatacc g                                        21

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
gtacttagtt attgttcgg                                           19

<210> SEQ ID NO 3
<211> LENGTH: 1631
<212> TYPE: DNA
<213> ORGANISM: Saccharomyces cerevisiae
<220> FEATURE:
<221> NAME/KEY: CDS
<222> LOCATION: (246)..(1580)
```

```
<400> SEQUENCE: 3
gcccatcttc aacaacaata ccgacttacc atcctatttg ctttgccctt ttcttttcc        60 actgcacttt gcatcggaag gcgttatcgg ttttgggttt agtgcctaaa cgagcagcga       120
gaacacgacc acgggctata taatggaaa gttaggacag gggcaaagaa taagagcaca        180
gaagaagaga aaagacgaag agcagaagcg gaaaacgtat acacgtcaca tatcacacac      240 acaca atg gga aag cta tta caa ttg gca ttg cat ccg gtc gag atg aag      290
      Met Gly Lys Leu Leu Gln Leu Ala Leu His Pro Val Glu Met Lys
      1               5                   10                  15 gca gct ttg aag ctg aag ttt tgc aga aca ccg cta ttc tcc atc tat        338
Ala Ala Leu Lys Leu Lys Phe Cys Arg Thr Pro Leu Phe Ser Ile Tyr
                20                  25                  30 gat cag tcc acg tct cca tat ctc ttg cac tgt ttc gaa ctg ttg aac        386
Asp Gln Ser Thr Ser Pro Tyr Leu Leu His Cys Phe Glu Leu Leu Asn
            35                  40                  45 ttg acc tcc aga tcg ttt gct gct gtg atc aga gag ctg cat cca gaa        434
Leu Thr Ser Arg Ser Phe Ala Ala Val Ile Arg Glu Leu His Pro Glu
        50                  55                  60 ttg aga aac tgt gtt act ctc ttt tat ttg att tta agg gct ttg gat        482
Leu Arg Asn Cys Val Thr Leu Phe Tyr Leu Ile Leu Arg Ala Leu Asp
65                  70                  75 acc atc gaa gac gat atg tcc atc gaa cac gat ttg aaa att gac ttg        530
Thr Ile Glu Asp Asp Met Ser Ile Glu His Asp Leu Lys Ile Asp Leu
80                  85                  90                  95 ttg cgt cac ttc cac gag aaa ttg tta act aaa tgg agt ttc gac           578
Leu Arg His Phe His Glu Lys Leu Leu Leu Thr Lys Trp Ser Phe Asp
                100                 105                 110 gga aat gcc ccc gat gtg aag gac aga gcc gtt ttg aca gat ttc gaa        626
Gly Asn Ala Pro Asp Val Lys Asp Arg Ala Val Leu Thr Asp Phe Glu
            115                 120                 125 tcg att ctt att gaa ttc cac aaa ttg aaa cca gaa tat caa gaa gtc        674
Ser Ile Leu Ile Glu Phe His Lys Leu Lys Pro Glu Tyr Gln Glu Val
        130                 135                 140 atc aag gag atc acc gag aaa atg ggt aat ggt atg gcc gac tac atc        722
Ile Lys Glu Ile Thr Glu Lys Met Gly Asn Gly Met Ala Asp Tyr Ile
    145                 150                 155 tta gat gaa aat tac aac ttg aat ggg ttg caa acc gtc cac gac tac        770
Leu Asp Glu Asn Tyr Asn Leu Asn Gly Leu Gln Thr Val His Asp Tyr
160                 165                 170                 175 gac gtg tac tgt cac tac gta gct ggt ttg gtc ggt gat ggt ttg acc       818
Asp Val Tyr Cys His Tyr Val Ala Gly Leu Val Gly Asp Gly Leu Thr
                180                 185                 190 cgt ttg att gtc att gcc aag ttt gcc aac gaa tct ttg tat tct aat        866
Arg Leu Ile Val Ile Ala Lys Phe Ala Asn Glu Ser Leu Tyr Ser Asn
            195                 200                 205 gag caa ttg tat gaa agc atg ggt ctt ttc cta caa aaa acc aac atc        914
Glu Gln Leu Tyr Glu Ser Met Gly Leu Phe Leu Gln Lys Thr Asn Ile
        210                 215                 220 atc aga gat tac aat gaa gat ttg gtc gat ggt aga tcc ttc tgg ccc        962
Ile Arg Asp Tyr Asn Glu Asp Leu Val Asp Gly Arg Ser Phe Trp Pro
225                 230                 235 aag gaa atc tgg tca caa tac gct cct cag ttg aag gac ttc atg aaa       1010
Lys Glu Ile Trp Ser Gln Tyr Ala Pro Gln Leu Lys Asp Phe Met Lys
240                 245                 250                 255 cct gaa aac gaa caa ctg ggg ttg gac tgt ata aac cac ctc gtc tta       1058
Pro Glu Asn Glu Gln Leu Gly Leu Asp Cys Ile Asn His Leu Val Leu
                260                 265                 270 aac gca ttg agt cat gtt atc gat gtg ttg act tat ttg gcc ggt atc       1106
Asn Ala Leu Ser His Val Ile Asp Val Leu Thr Tyr Leu Ala Gly Ile
```

```
                Asn Ala Leu Ser His Val Ile Asp Val Leu Thr Tyr Leu Ala Gly Ile
                                275                 280                 285 cac gag caa tcc act ttc caa ttt tgt gcc att ccc caa gtt atg gcc              1154
His Glu Gln Ser Thr Phe Gln Phe Cys Ala Ile Pro Gln Val Met Ala
                290                 295                 300 att gca acc ttg gct ttg gta ttc aac aac cgt gaa gtg cta cat ggc              1202
Ile Ala Thr Leu Ala Leu Val Phe Asn Asn Arg Glu Val Leu His Gly
305                 310                 315 aat gta aag att cgt aag ggt act acc tgc tat tta att ttg aaa tca              1250
Asn Val Lys Ile Arg Lys Gly Thr Thr Cys Tyr Leu Ile Leu Lys Ser
320                 325                 330                 335 agg act ttg cgt ggc tgt gtc gag att ttt gac tat tac tta cgt gat              1298
Arg Thr Leu Arg Gly Cys Val Glu Ile Phe Asp Tyr Tyr Leu Arg Asp
                340                 345                 350 atc aaa tct aaa ttg gct gtg caa gat cca aat ttc tta aaa ttg aac              1346
Ile Lys Ser Lys Leu Ala Val Gln Asp Pro Asn Phe Leu Lys Leu Asn
            355                 360                 365 att caa atc tcc aag atc gaa cag ttt atg gaa gaa atg tac cag gat              1394
Ile Gln Ile Ser Lys Ile Glu Gln Phe Met Glu Glu Met Tyr Gln Asp
        370                 375                 380 aaa tta cct cct aac gtg aag cca aat gaa act cca att ttc ttg aaa              1442
Lys Leu Pro Pro Asn Val Lys Pro Asn Glu Thr Pro Ile Phe Leu Lys
385                 390                 395 gtt aaa gaa aga tcc aga tac gat gat gaa ttg gtt cca acc caa caa              1490
Val Lys Glu Arg Ser Arg Tyr Asp Asp Glu Leu Val Pro Thr Gln Gln
400                 405                 410                 415 gaa gaa gag tac aag ttc aat atg gtt tta tct atc atc ttg tcc gtt              1538
Glu Glu Glu Tyr Lys Phe Asn Met Val Leu Ser Ile Ile Leu Ser Val
                420                 425                 430 ctt ctt ggg ttt tat tat ata tac act tta cac aga gcg tga                      1580
Leu Leu Gly Phe Tyr Tyr Ile Tyr Thr Leu His Arg Ala
                435                 440 agtctgcgcc aaataacata aacaaacaac tccgaacaat aactaagtac t                     1631

<210> SEQ ID NO 4
<211> LENGTH: 444
<212> TYPE: PRT
<213> ORGANISM: Saccharomyces cerevisiae

<400> SEQUENCE: 4

Met Gly Lys Leu Leu Gln Leu Ala Leu His Pro Val Glu Met Lys Ala
1               5                   10                  15

Ala Leu Lys Leu Lys Phe Cys Arg Thr Pro Leu Phe Ser Ile Tyr Asp
                20                  25                  30

Gln Ser Thr Ser Pro Tyr Leu Leu His Cys Phe Glu Leu Leu Asn Leu
            35                  40                  45

Thr Ser Arg Ser Phe Ala Ala Val Ile Arg Glu Leu His Pro Glu Leu
        50                  55                  60

Arg Asn Cys Val Thr Leu Phe Tyr Leu Ile Leu Arg Ala Leu Asp Thr
65                  70                  75                  80

Ile Glu Asp Asp Met Ser Ile Glu His Asp Leu Lys Ile Asp Leu Leu
                85                  90                  95

Arg His Phe His Glu Lys Leu Leu Leu Thr Lys Trp Ser Phe Asp Gly
                100                 105                 110

Asn Ala Pro Asp Val Lys Asp Arg Ala Val Leu Thr Asp Phe Glu Ser
            115                 120                 125

Ile Leu Ile Glu Phe His Lys Leu Lys Pro Glu Tyr Gln Glu Val Ile
        130                 135                 140
```

```
-continued

Lys Glu Ile Thr Glu Lys Met Gly Asn Gly Met Ala Asp Tyr Ile Leu
145                 150                 155                 160

Asp Glu Asn Tyr Asn Leu Asn Gly Leu Gln Thr Val His Asp Tyr Asp
            165                 170                 175

Val Tyr Cys His Tyr Val Ala Gly Leu Val Gly Asp Gly Leu Thr Arg
            180                 185                 190

Leu Ile Val Ile Ala Lys Phe Ala Asn Glu Ser Leu Tyr Ser Asn Glu
        195                 200                 205

Gln Leu Tyr Glu Ser Met Gly Leu Phe Leu Gln Lys Thr Asn Ile Ile
        210                 215                 220

Arg Asp Tyr Asn Glu Asp Leu Val Asp Gly Arg Ser Phe Trp Pro Lys
225                 230                 235                 240

Glu Ile Trp Ser Gln Tyr Ala Pro Gln Leu Lys Asp Phe Met Lys Pro
            245                 250                 255

Glu Asn Glu Gln Leu Gly Leu Asp Cys Ile Asn His Leu Val Leu Asn
            260                 265                 270

Ala Leu Ser His Val Ile Asp Val Leu Thr Tyr Leu Ala Gly Ile His
        275                 280                 285

Glu Gln Ser Thr Phe Gln Phe Cys Ala Ile Pro Gln Val Met Ala Ile
        290                 295                 300

Ala Thr Leu Ala Leu Val Phe Asn Asn Arg Glu Val Leu His Gly Asn
305                 310                 315                 320

Val Lys Ile Arg Lys Gly Thr Thr Cys Tyr Leu Ile Leu Lys Ser Arg
            325                 330                 335

Thr Leu Arg Gly Cys Val Glu Ile Phe Asp Tyr Tyr Leu Arg Asp Ile
            340                 345                 350

Lys Ser Lys Leu Ala Val Gln Asp Pro Asn Phe Leu Lys Leu Asn Ile
        355                 360                 365

Gln Ile Ser Lys Ile Glu Gln Phe Met Glu Glu Met Tyr Gln Asp Lys
        370                 375                 380

Leu Pro Pro Asn Val Lys Pro Asn Glu Thr Pro Ile Phe Leu Lys Val
385                 390                 395                 400

Lys Glu Arg Ser Arg Tyr Asp Asp Glu Leu Val Pro Thr Gln Gln Glu
            405                 410                 415

Glu Glu Tyr Lys Phe Asn Met Val Leu Ser Ile Ile Leu Ser Val Leu
            420                 425                 430

Leu Gly Phe Tyr Tyr Ile Tyr Thr Leu His Arg Ala
        435                 440
```